United States Patent [19]

Wenk et al.

[11] 4,451,462
[45] May 29, 1984

[54] METHOD OF TREATING INFLAMMATION AND PAIN USING HETERAMINO BENZOFURANS

[75] Inventors: Paul Wenk, Allschwil; Werner Breitenstein; Marcus Baumann, both of Basel, all of Switzerland

[73] Assignee: Ciba-Geigy Corporation, Ardsley, N.Y.

[21] Appl. No.: 542,334

[22] Filed: Oct. 17, 1983

Related U.S. Application Data

[63] Continuation of Ser. No. 435,595, Oct. 21, 1982, Pat. No. 4,426,380.

[30] Foreign Application Priority Data

Oct. 28, 1981 [CH] Switzerland .................. 6882/81

[51] Int. Cl.³ .................. A61K 31/445; A61K 31/535
[52] U.S. Cl. .................. 424/248.55; 424/246; 424/248.5; 424/248.52; 424/250; 424/256; 424/267; 424/270; 424/272; 424/273 R; 424/274; 424/279
[58] Field of Search .................. 424/246, 248.5, 248.52, 424/248.55, 250, 256, 267, 270, 272, 273 R, 274, 279

[56] References Cited

U.S. PATENT DOCUMENTS 3,829,446  8/1974  Kadin .................. 549/304

Primary Examiner—Robert W. Ramsuer
Attorney, Agent, or Firm—Michael W. Glynn

[57] ABSTRACT

The invention relates to novel furans, especially benzofuranones of the general formula

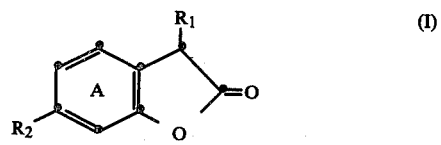

in which $R_1$ represents hydrogen or an aliphatic radical, $R_2$ represents an amino group di-substituted by a divalent hydrocarbon radical, and the aromatic ring A may be additionally substituted, and their salts and/or isomers, processes for the manufacture of compounds of the formula (I) and their salts and isomers, pharmaceutical preparations containing these compounds, and their use as the active ingredients of anti-inflammatory agents or analgesics and/or for the manufacture of pharmaceutical preparations.

11 Claims, No Drawings

METHOD OF TREATING INFLAMMATION AND PAIN USING HETERAMINO BENZOFURANS

This is a continuation of application Ser. No. 435,595 filed Oct. 21, 1982 now U.S. Pat. No. 4,426,380.

The invention relates to novel furans, especially benzofuranones of the general formula

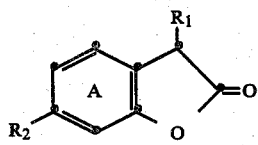

(I)

in which $R_1$ represents hydrogen or an aliphatic radical, $R_2$ represents an amino group di-substituted by a divalent hydrocarbon radical, and the aromatic ring A may be additionally substituted, and their salts and/or isomers, processes for the manufacture of compounds of the formula (I) and their salts and isomers, pharmaceutical preparations containing these compounds, and their use as the active ingredients of medicaments and/or for the manufacture of pharmaceutical preparations.

Isomers of compounds of the formula (I) are, for example, the 2-hydroxybenzo[b]furan compounds of the formula

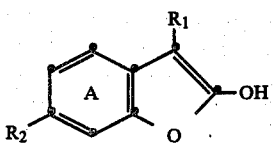

(I')

which are in tautomeric equilibrium with the 2,3-dihydro-2-oxobenzo[b]furan derivatives of the formula (I).

An aliphatic radical $R_1$ is, especially, saturated and unsubstituted and represents, especially, a lower alkyl radical.

The aromatic ring A may be additionally mono- or poly-substituted by an aliphatic radical, such as lower alkyl, hydroxy-lower alkyl, halo-lower alkyl, lower alkenyl, or optionally branched, especially bridging two adjacent carbon atoms, 3- or 4-membered alkylene having from 3 to 8 carbon atoms, lower alkoxy, lower alkylthio, lower alkanesulphinyl, lower alkane-sulphonyl, hydroxy, halogen, lower alkanoyloxy, lower alkanoyl and/or nitro, or, except for $R_2$, it may be unsubstituted.

An amino group disubstituted by a divalent hydrocarbon radical has, as that radical, a divalent aliphatic radical which may also be interrupted by aza, N-lower alkylaza, oxa or thia, such as lower alkylene or lower alkenylene, or lower alkylene or lower alkenylene each interrupted by aza, N-lower alkylaza, oxa or thia; lower alkylene and lower alkenylene may also be branched. Such cyclic amines $R_2$ may also have one or two orthofused benzo systems. $R_2$ preferably represents lower alkylene-, lower alkenylene-, aza-lower alkylene-, N'-lower alkylaza-lower alkylene, aza-lower alkenylene-, N'-lower alkylaza-lower alkenylene-, oxa- or thia-lower alkylene- or oxa- or thia-lower alkenylene-amino, each being 5- to 8-membered; lower alkylene and lower alkenylene may also be branched and accordingly may have from 4 to 14, preferably from 4 to 7, carbon atoms.

There may be mentioned as examples of such radicals $R_2$: pyrrolidin-1-yl, 2- or 3-pyrrolin-1-yl, pyrrol-1-yl, piperidin-1-yl, azepin-1-yl, imidazolidin-1-yl, 2-, 3- or 4-imidazolin-1-yl, oxazolidin-3-yl, 4-oxazolin-3-yl, thiazolidin-3-yl, 4-thiazolidin-3-yl, piperazin-1-yl, morpholin-4-yl, thiomorpholin-4-yl, 3-methylimidazolidin-1-yl and 4-methylpiperazin-1-yl.

$R_2$ also represents lower alkylene- or lower alkenylene-amino having one or two ortho-fused benzo systems, such as indol-1-yl, indolin-1-yl, isoindol-2-yl, isoindolin-2-yl, carbazol-9-yl or β-carbolin-9-yl.

Hereinbefore and hereinafter, organic radicals and compounds designated "lower" should preferably be understood as being those that contain up to and including 7, especially up to and including 4, carbon atoms.

The general definitions used within the framework of the present test have, especially, the following meanings:

Lower alkyl is, for example, methyl, ethyl, n-propyl, isopropyl, n-butyl, isobutyl, sec.-butyl, tert.-butyl and also includes, correspondingly, pentyl, hexyl and heptyl radicals.

Hydroxy-lower alkyl is, for example, hydroxymethyl, 2-hydroxyethyl or 2- or 3-hydroxypropyl.

Halo-lower alkyl is, for example, chloromethyl or trifluoromethyl.

Lower alkenyl is, for example, vinyl, 1- or 2-propenyl, 1-, 2- or 3-butenyl or butadien-1,3-yl.

3- or 4-membered alkylene has, especially, from 3 to 8 carbon atoms and is straight-chained, such as tri- or tetra-methylene, or branched, such as 2,4-butylene, 1,4- or 2,4-pentylene or 2-methyl-1,3-propylene.

Lower alkoxy is, for example, methoxy, ethoxy, n-propoxy, isopropoxy, n-butoxy, isobutoxy, sec.-butoxy, tert.-butoxy and also includes, correspondingly, pentyloxy, hexyloxy and heptyloxy radicals.

Lower alkylthio is, for example, methyl-, ethyl-, n-propyl-, isopropyl-, n-butyl-, isobutyl-, sec.-butyl- or tert.-butyl-thio.

Lower alkane-sulphinyl or -sulphonyl is, for example, methane-, ethane-, n-propane- or isopropanesulphinyl or -sulphonyl.

Halogen is, for example, halogen having an atomic number of up to and including 35, such as fluorine, chlorine or bromine, and also includes iodine.

Lower alkanoyloxy is, for example, acetoxy, propionyloxy, butyryloxy, isobutyryloxy, sec.- or tert.-butyryloxy.

Lower alkanoyl is, for example, acetyl, propionyl, butyryl, isobutyryl or tert.-butyryl.

3- or 4-membered alkylene is, for example, tri- or tetra-methylene.

Lower alkylene is, for example, 4- to 7-membered lower alkylene and has, for example, from 4 to 10, especially from 4 to 6, carbon atoms, such as tetra-, penta- or hexa-methylene, also heptamethylene.

Lower alkenylene has one or two double bonds and is, for example, 4- to 7-membered lower alkenylene, for example having from 4 to 10, especially from 4 to 6, carbon atoms, such as but-2-en-1,4-ylene, buta-1,3-dien-1,4-ylene, pent-2-en-1,5-ylene, penta-1,3-dien-1,5-ylene, penta-1,4-dien-1,5-ylene, or hexa-2,4-dien-2,4-ylene.

Lower alkylene interrupted by aza or N-lower alkylaza is, for example, 4- to 7-membered monoaza- or N'-lower alkylmonoaza-lower alkylene, such as 2-azatetramethylene, 3-azapentamethylene or 3-methylazapentamethylene.

Lower alkylene interrupted by oxa or thia is, for example, monooxa- or monothia-lower alkylene, such as 3-oxa- or 3-thia-pentamethylene.

Lower alkenylene that has one or two double bonds and that is interrupted by aza or N-lower alkylaza is, for example, 2-azabuten-1-ylene, 2-azabuten-2-ylene, 2-azabuten-3-ylene, 2-methylazabuten-3-ylene or 2-azabutadien-1,3-ylene.

Salts of compounds of the formula (I) according to the invention are preferably pharmaceutically acceptable salts, such as pharmaceutically acceptable acid addition salts. These are formed, for example, with strong inorganic acids, such as mineral acids, for example sulphuric acid, phosphoric acid, or hydrohalic acids, with strong organic carboxylic acids, such as lower alkanecarboxylic acids, for example acetic acid, such as optionally unsaturated dicarboxylic acids, for example oxalic, malonic, maleic or fumaric acid, or such as hydroxycarboxylic acids, for example tartaric acid or citric acid, or with sulphonic acids, such as lower alkane- or optionally substituted benzene-sulphonic acids, for example methane- or p-toluenesulphonic acid. If the 1,2-phenylene radical Ph has hydroxy as substituent, corresponding compounds can form salts with bases. Suitable salts with bases are, for example, corresponding alkali metal or alkaline earth metal salts, for example sodium, potassium, or magnesium salts, and pharmaceutically acceptable transition metal salts, such as zinc or copper salts.

Isomers of the formula (I) are especially in the form of structural isomers. If, for example, compounds of the formula (I) have chiral carbon atoms, they may be in the form of diastereoisomers, diastereoisomeric mixtures, or racemates or in the form of a pure enantiomer, while, for example, the tautomers of the formula (I') form, for example, geometric isomers, for example E/Z isomers.

The compounds of the formula (I) have valuable pharmacological properties. They have, especially, a pronounced anti-inflammatory action which can be demonstrated, for example, by reduction of the carrageenin-induced paw oedema in rats at a dose of approximately 0.1 mg/kg p.o. and above analogously to the method described by Pasquale et al, Ag. and Actions, 5, 256 (1975), and in the adjuvant-arthritis model in rats at a dose of approximately 1,0 mg/kg p.o. and above analogously to the method described by L. Risterer et al., Pharmacology, 2, 288 (1969). In addition, compounds of the formula (I) inhibit, in vitro, at a concentration of approximately 10 $\mu$mol/l and above prostaglandin synthesis from arachidonic acid analogously to the method described by H. L. White et al., Prostaglandins, 7, 123 (1974).

The compounds of the formula (I) also have a distinct antinociceptive activity that can be derived, for example, from the reduction, described by L. C. Hendershot et al., J. Pharmacol. exp. Therap. 125, 237 (1959), of the phenyl-p-benzoquinone-induced writhing syndrome in mice at a dose of approximately 0.1 mg/kg p.o. and above.

Furthermore, the compounds of the formula (I) have the ability to absorb from the range of the UV spectrum the rays producing erythema on the epidermis (between 290 and 320 nm) while the substances are transmitted by the tanning rays of from approximately 320 to approximately 400 nm.

Consequently, these compounds can be used as anti-inflammatory agents, (peripheral) analgesics and/or light-screening agents, for example for cosmetic purposes.

The invention relates, for example, to compounds of the formula (I) in which $R_1$ represents hydrogen or a saturated and unsubstituted aliphatic radical, $R_2$ represents an amino group di-substituted by a divalent aliphatic radical which may also be interrupted by aza, N-lower alkylaza, oxa or thia, and the aromatic ring A is additionally mono- or poly-substituted by an aliphatic radical, lower alkoxy, lower alkylthio, lower alkanesulphinyl, lower alkanesulphonyl, hydroxy, halogen, lower alkanoyloxy, lower alkanoyl and/or nitro, or, except for $R_2$, is unsubstituted, and their salts, especially pharmaceutically acceptable salts, and isomers.

The invention relates, for example, to compounds of the formula (I) in which $R_1$ represents hydrogen or lower alkyl, $R_2$ represents an amino group disubstituted by lower alkylene, lower alkenylene, aza-lower alkylene, N'-lower alkylaza-lower alkylene, aza-lower alkenylene, N-lower alkylaza-lower alkenylene, oxa- or thia-lower alkylene or oxa- or thia-lower alkenylene, wherein lower alkylene or lower alkenylene respectively in each case has from 4 to 10 carbon atoms and may also be branched and also ortho-fused with one or two benzo systems, and the aromatic ring A is additionally mono- or polysubstituted by lower alkyl, hydroxy-lower alkyl, halo-lower alkyl, lower alkenyl, optionally branched 3- or 4-membered alkylene, lower alkoxy, lower alkylthio, lower alkanesulphinyl, lower alkanesulphonyl, hydroxy, halogen, lower alkanoyloxy, lower alkanoyl and/or nitro or, except for $R_2$, is unsubstituted, and their salts, especially pharmaceutically acceptable salts, and isomers.

The invention relates, for example, to compounds of the formula (I) in which $R_1$ represents hydrogen or lower alkyl, $R_2$ represents an amino group substituted by lower alkylene or lower alkenylene, or by lower alkylene interrupted by aza, N-lower alkylaza, or by lower alkenylene interrupted by aza or N-lower alkylaza, and the aromatic ring A may be additionally substituted by lower alkyl, lower alkoxy, hydroxy, halogen, lower alkanoyloxy, 3- or 4-membered alkylene and/or trifluoromethyl, and their salts, especially pharmaceutically acceptable salts, and isomers.

The invention relates especially to compounds of the formula

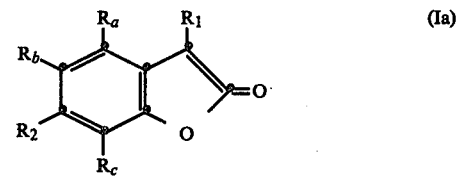

in which $R_1$ represents hydrogen or lower alkyl, such as methyl, $R_2$ represents, in each case 5- to 8-membered, lower alkyleneamino, such as pyrrolidin-1-yl, lower alkenyleneamino, such as pyrrol-1-yl or 3-pyrrolin-1-yl, aza-lower alkyleneamino, such as piperazin-1-yl, N'-lower alkylaza-lower alkyleneamino, such as 4-methylpiperazin-1-yl, aza-lower alkenyleneamino, such as imidazol-1-yl, N'-lower alkylaza-lower alkenyleneamino, such as 3-methylimidazol-1-yl, oxa- or thia-lower alkyleneamino, such as morpholin-4-yl or thiomorpholin-4-yl, isoindol-2-yl, isoindolin-2-yl, indolin-1-yl or indol-1-yl, and $R_a$, $R_b$ and $R_c$ each represents, independently of one another, hydrogen, lower alkyl, such as methyl, hydroxy-lower alkyl, such as hydroxymethyl, halo-lower alkyl, such as trifluoromethyl, lower alkenyl, such as 2-propenyl, lower alkoxy, such as methoxy, lower alkylthio, such as methylthio, lower alkanesulphinyl, such as methanesulphinyl, lower alkanesulphonyl, such as methanesulphonyl, hydroxy, halogen, such as bromine or chlorine, lower alkanoyloxy, such as acetoxy, lower alkanoyl, such as acetyl, or nitro, or $R_a$ together with $R_b$ represents 3- or 4-membered alkylene, such as tetramethylene, and $R_c$ has the meanings given above for $R_c$, and their salts, especially pharmaceutically acceptable salts, and isomers.

The invention relates especially to compounds of the formula (Ia) in which $R_1$ represents hydrogen or lower alkyl, such as methyl, $R_2$ represents, in each case 5- to 8-membered, lower alkyleneamino, such as pyrrolidin-1-yl, lower alkenyleneamino, such as pyrrol-1-yl, monoaza-lower alkyleneamino, such as piperazin-1-yl, N'-lower alkylmonoaza-lower alkyleneamino, such as 4-methylpiperazin-1-yl, monooxa-lower alkyleneamino, such as morpholin-4-yl, monothia-lower alkyleneamino, such as thiomorpholin-4-yl, monoaza-lower alkenyleneamino, such as imidazol-1-yl, or N'-lower alkyleneaza-lower alkenyleneamino, such as 3-methylimidazol-1-yl, and $R_a$, $R_b$ and $R_c$ each represents, independently of one another, hydrogen, lower alkyl, such as methyl, lower alkoxy, such as methoxy, hydroxy, halogen, such as chlorine, lower alkanoyloxy, such as acetoxy, or trifluoromethyl, or $R_a$ together with $R_b$ represents 3- or 4-membered alkylene, such as tetramethylene, and $R_c$ has the meanings given above for $R_c$, and their salts, especially pharmaceutically acceptable salts, and isomers.

The invention relates more especially to compounds of the formula (Ia) in which $R_1$ represents hydrogen or lower alkyl having up to and including 4 carbon atoms, such as methyl, $R_2$ represents 5- to 8-membered lower alkyleneamino having from 4 to 10 carbon atoms, such as pyrrolidin-1-yl or 3,4-dimethylpyrrolidin-1-yl, 5- to 8-membered lower alkenyleneamino having one or two double bonds and from 4 to 10 carbon atoms, such as 3-pyrrolin-1-yl or pyrrol-1-yl, monooxa-lower alkyleneamino having from 4 to 7 carbon atoms, such as morpholin-4-yl, indolin-1-yl or indol-1-yl, and $R_a$ and $R_b$ each represents, independently of the other, hydrogen, lower alkyl, especially having up to and including 4 carbon atoms, such as methyl, or halogen, especially having an atomic number of up to and including 35, such as chlorine or bromine, or $R_a$ and $R_b$ together represent 3- or 4-membered alkylene, such as tetramethylene, and $R_c$ represents hydrogen, and their salts, especially pharmaceutically acceptable salts, and isomers.

The invention relates more especially to compounds of the formula (Ia) in which $R_1$ represents hydrogen or lower alkyl, especially having up to and including 4 carbon atoms, such as methyl, $R_2$ represents 5- to 8-membered lower alkyleneamino, such as pyrrolidin-1-yl, 5- to 8-membered lower alkenyleneamino, such as pyrrol-1-yl, or monooxa-lower alkyleneamino, such as morpholin-4-yl, and $R_a$ and $R_b$ each represents, independently of the other, hydrogen, lower alkyl, especially having up to and including 4 carbon atoms, such as methyl, or halogen, especially having an atomic number of up to and including 35, such as chlorine or bromine, or $R_a$ together with $R_b$ represents 3- or 4-membered alkylene, such as tetramethylene, and $R_c$ represents hydrogen, and their salts, especially pharmaceutically acceptable salts, and isomers.

The invention relates most especially to compounds of the formula (Ia) in which $R_1$ represents hydrogen or lower alkyl having up to and including 4 carbon atoms, such as methyl, $R_2$ represents 5- to 8-membered lower alkyleneamino, such as pyrrolidin-1-yl, 5- to 8-membered lower alkenyleneamino, such as pyrrol-1-yl, or monooxa-lower alkyleneamino, such as morpholin-4-yl, and $R_a$ and $R_c$ represent hydrogen and $R_b$ represents hydrogen, lower alkyl having up to and including 4 carbon atoms, especially methyl, or halogen having an atomic number of up to and including 35, especially chlorine or bromine, and their salts, especially pharmaceutically acceptable salts, and isomers.

The invention relates first and foremost to compounds of the formula (Ia) in which $R_1$ represents hydrogen or lower alkyl, having up to and including 4 carbon atoms, especially methyl, $R_2$ represents 1-pyrrolyl, 3-pyrrolin-1-yl, pyrrolidin-1-yl or piperidin-1-yl, $R_a$ and $R_c$ each represents hydrogen, and $R_b$ represents lower alkyl having up to and including 4 carbon atoms, especially methyl, or halogen having an atomic number of up to and including 35, especially chlorine or bromine, and their salts, especially pharmaceutically acceptable salts, and isomers.

The invention relates more especially to compounds of the formula (Ia) in which $R_1$ represents hydrogen or lower alkyl, having up to and including 4 carbon atoms, especially methyl, $R_2$ represents 1-pyrrolyl, 4-morpholinyl, 3-pyrrolin-1-yl, or unbranched 4- to 6-membered alkyleneamino, such as piperidin-1-yl, $R_a$ and $R_c$ each represents hydrogen and $R_b$ represents hydrogen, lower alkyl having up to and including 4 carbon atoms, especially methyl, or halogen having an atomic number of up to and including 35, especially chlorine or bromine, or $R_c$ represents hydrogen and $R_a$ and $R_b$ together represent 3- or 4-membered alkylene, especially tetramethylene, or one or the radicals $R_a$ and $R_b$ represents halogen having an atomic number of up to and including 35, especially bromine, and the other represents lower alkyl having up to and including 4 carbon atoms, especially methyl, and their salts, especially pharmaceutically acceptable salts, and isomers.

The invention relates first and foremost to compounds of the formula (Ia) in which $R_1$ represents lower alkyl having up to and including 4 carbon atoms, especially methyl, $R_2$ represents 5- to 8-membered lower alkenyleneamino, especially pyrrol-1-yl, $R_a$ and $R_c$ represent hydrogen and $R_b$ represents lower alkyl having up to and including 4 carbon atoms, especially methyl, and their salts, especially pharmaceutically acceptable salts, and their isomers.

The invention relates especially to the novel compounds mentioned in the Examples, their salts, especially pharmaceutically acceptable salts, and isomers, and also to the processes for their manufacture described in the Examples.

The compounds of the present invention are manufactured in a manner known per se, for example by (a) cyclising a compound of the formula

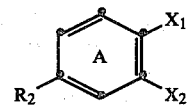

(II)

or a salt thereof, in which $X_1$ represents a group of the formula $-CH(R_1)-X_3$ and $X_3$ represents carboxy or functionally modified carboxy and $X_2$ represents hydroxy or functionally modified hydroxy, or in which $X_1$ represents hydrogen and $X_2$ represents a group of the formula —O—CO—CH(R₁)—X₄ in which X₄ represents hydroxy or functionally modified hydroxy, or (b) in a compound of the formula

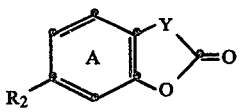
(III)

or a salt or isomer thereof, in which Y represents a radical that can be converted into the group of the formula >CH(R₁), converting Y into the group of the formula >CH(R₁), or (c) in a compound of the formula

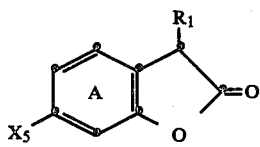
(IV)

or a salt or isomer thereof, in which X₅ represents a group that can be converted into R₂, converting X₅ into R₂, or (d) in a compound of the formula

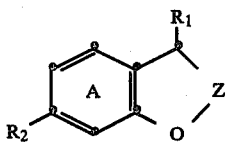
(V)

or a salt thereof, in which Z represents a group that can be converted into the carbonyl group, converting Z into the carbonyl group, or (e) in a compound of the formula

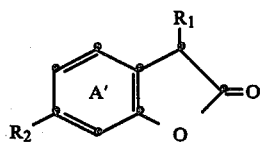
(VI)

or a salt thereof, in which the ring A' is a ring that can be converted into the ring A, converting the ring A' into the ring A, and/or, if desired, converting a salt obtainable according to the process into the free compound or into a different salt, converting a free compound obtainable according to the process into a different free compound or into a salt and/or, if desired, separating an isomeric mixture obtainable according to the process into its components.

Re variant (a):

Starting materials of the formula II may be in the form of salts, for example acid addition salts, or, if the group X₃ contains carboxy or the aromatic ring A contains hydroxy, they may be in the form of salts with bases.

Functionally modified carboxy X₃ represents, especially, functionally modified carboxy containing an oxo group, such as esterified, amidated or anhydridised carboxy, also an orthocarboxylic acid ester grouping, an orthoanhydride grouping or optionally functionally modified thiocarboxy. Esterified carboxy should be understood as meaning carboxy esterified, for example, by an optionally substituted alcohol, such as optionally substituted alkanol or cycloalkanol, for example lower alkanol or 4- to 7-membered cycloalkanol, or by an optionally substituted phenol, such as lower alkoxycarbonyl, for example ethoxycarbonyl, cycloalkoxycarbonyl, for example cyclohexyloxycarbonyl, or phenoxycarbonyl. Anhydridised carboxy is, for example, a symmetric or mixed anhydride with inorganic acids, such as hydrohalic acids, or with organic carboxylic acids, such as optionally substituted lower alkanecarboxylic acids, for example halocarbonyl, for example chlorocarbonyl, or lower alkanoyloxycarbonyl, for example acetoxycarbonyl. Amidated carboxy contains as the amino group, for example, a free or mono- or disubstituted amino group. Unsubstituted carbamoyl is derived from ammonia and mono- or di-substituted carbamoyl is derived from primary or secondary amine, respectively. Suitable examples of corresponding amidated carboxy are, for example, carbamoyl, carbamoyl mono-substituted by optionally substituted phenyl, carbamoyl mono- or di-substituted by lower alkyl or carbamoyl di-substituted by 4- to 7-membered alkylene or 4- to 7-membered oxa-, aza-, N-lower alkylaza- or thiaalkylene, such as lower alkyleneaminocarbonoyl, morpholino- or thiomorpholino-carbonoyl, or carbamoyl mono- or di-substituted by lower alkyl optionally containing aryl, such as N-mono- or N-di-lower alkylcarbamoyl.

Orthoester groupings are, for example, trialkoxymethyl groupings, such as tri-lower alkoxymethyl groups. Corresponding orthoanhydride groupings are, for example, tri-halomethyl compounds.

Functionally modified hydroxy X₂ or X₄ should be understood as meaning, for example, functionally modified hydroxy containing an oxy group, such as esterified hydroxy or etherified hydroxy. Esterified hydroxy is, for example, hydroxy esterified by an organic carboxylic acid, such as lower alkanecarboxylic acid, and represents, for example, lower alkanoyloxy, for example acetoxy. Etherified hydroxy is, for example, alkoxy, such as lower alkoxy, for example methoxy or ethoxy. X₄ also represents hydroxy esterified by a mineral acid, such as hydrohalic acid, or by a sulphonic acid, such as lower alkane- or optionally substituted benzene-sulphonic acid, for example halogen, methane- or p-toluene-sulphonyloxy.

The cyclisation of compounds of the formula (II) is carried out in customary manner, especially in the manner known from the literature for analogous reactions. Thus, the operation is carried out if necessary in the presence of a catalytic agent, such as an acidic agent. Suitable as acidic agents are, for example, strong inorganic or organic protonic acids, such as mineral acids, for example hydrohalic acids, sulphuric acid or polyphosphoric acid, sulphonic acids, such as alkane- or optionally substituted benzene-sulphonic acids, for example methane- or p-toluenesulphonic acids, or organic carboxylic acids, such as lower alkanecarboxylic acids, for example glacial acetic acid. It is also possible to use Lewis acids for the cyclisation of compounds of the formula (II), especially for the cyclisation of compounds of the formula (II) in which X₁ represents hydrogen and X₂ represents a group of the formula —O—CO—CH(R₁)—X₄. There are used as Lewis acids, i.e. electronacceptors, for example compounds of elements of the third and fifth main groups and also of the second and eighth sub-groups of the Periodic Table. There come into consideration especially halides of boron, aluminium, tin, antimony and iron, for example boron trifluoride, aluminium chloride, tin(IV) chloride, zinc chloride and iron(III) chloride, and also lower alkanoates of thallium, such as thallium(III) acetate. The cyclisation of compounds of the formula (II) is carried out under inert conditions, such as under inert gas, for example nitrogen or argon, in the presence or absence of an inert solvent and/or under pressure, for example in a closed apparatus, and at a suitable reaction temperature, for example at from approximately 0° C. to approximately 250° C. Solvents are, for example, those that bind the water formed during the reaction, such as acetic anhydride, or with the aid of which the water can be removed from the reaction mixture, for example by azeotropic distillation, such as toluene, benzene or xylenes, also non-polar solvents, such as ether, methylene chloride or chloroform.

In a preferred embodiment of the cyclisation, compounds of the formula (II) are used in which $X_1$ represents a group of the formula $-CH(R_1)-X_3$ in which $X_3$ is carboxy, and $X_2$ represents hydroxy. In this case it is sufficient to use catalytically active acids in traces. If the operation is carried out in the absence of corresponding protonic acids, the water being formed during the reaction is advantageously removed from the reaction mixture, for example by azeotropic distillation, or bound by suitable water-binding agents, such as alkanecarboxylic acid anhydrides, for example acetic anhydride, or by substituted diimides, such as dicycloalkyl carbodiimides, for example dicyclohexyl carbodiimide.

In a further preferred embodiment, compounds of the formula (II) in which $X_1$ represents a group of the formula $-CH(R_1)-X_3$ and $X_3$ represents carboxy or esterified or amidated carboxy and $X_2$ represents hydroxy etherified by an alkanol are cyclised by heating with hydriodic acid or hydrobromic acid and a lower alkanecarboxylic acid anhydride, especially acetic anhydride, directly and without isolating intermediates, to form the corresponding compounds of the formula (I).

The starting materials of the formula (II) or their salts can be obtained according to processes known per se. For example, compounds of the formula (IIa)

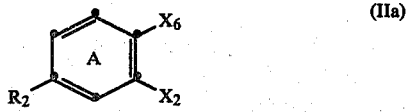

or salts thereof, in which $X_6$ represents a group of the formula $R_1-CH_2-CO-$, are used as starting materials and are reacted with ammonium polysulphide under pressure or with sulphur and a primary or secondary amine, advantageously with morpholine or thiomorpholine. In a resulting compound of the formula (II) in which $X_1$ represents a group of the formula $-CH(R_1)-X_3$, $R_1$ represents hydrogen and $X_3$ represents correspondingly substituted thiocarbamoyl or carbamoyl, or ammonium carboxylate, $X_3$ is converted by solvolysis, for example by hydrolysis, into carboxy, or especially by alcoholysis into a correspondingly esterified carboxy group $X_3$.

In an optional additional reaction, compounds of the formula (IIa) in which $X_6$ is a group of the formula $R_1-CH_2-CO$ and $R_1$ is hydrogen can be converted into compounds of the formula (IIa) in which $X_6$ is a group of the formula $R_1-CH_2-CO$ and $R_1$ represents an aliphatic radical. This is generally carried out by treatment with a reactive esterified aliphatic alcohol, such as a lower alkyl halide, in the presence of a strong base, such as an alkali metal alcoholate, for example sodium methoxide. Compounds of the formula (II) in which $X_2$ represents reactive esterified hydroxy and $X_1$ is a group of the formula $-CH(R_1)-X_3$ and $X_3$, for example, represents functionally modified carboxy are advantageously reacted under hydrolytic conditions in situ without isolation to form corresponding compounds of the formula (I). In compounds of the formula (II) in which $X_2$ represents etherified hydroxy, the ether grouping is advantageously cleaved, for example by treatment with a strong acid, such as a hydrohalic acid, for example hydriodic acid, or with pyridine hydrochloride.

In a further, especially preferred embodiment of the cyclisation process, compounds of the formula (Ia) in which $R_1$ represents methyl and $R_a$, $R_b$ and $R_c$ each represents hydrogen or lower alkyl, or $R_a$ and $R_b$ together represent 3- or 4-membered alkylene and $R_c$ has the meaning given above, are obtained by reacting compounds of the formula

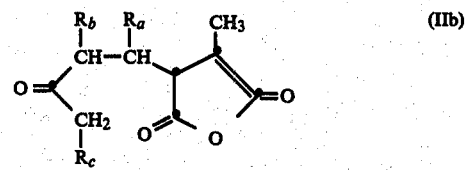

which are known or can be manufactured as described below, with amines of the formula $R_2-H$ (IIc) or their acid addition salts. In this case, compounds of the formula (II) in which $X_1$ represents a group of the formula $-CH(CH_3)-COOH$ and $X_2$ represents hydroxy may be formed for example intermediately and cyclise directly under the reaction conditions to form the corresponding compounds of the formula (Ia).

The reaction is carried out, for example, at elevated temperature, for example in the melt or at the reflux temperature of the solvent, for example in a temperature range of from approximately 80° C. to approximately 200° C. Suitable inert solvents are, for example, higher-boiling hydrocarbons, such as aromatic hydrocarbons, for example benzene, toluene or xylenes. The amines of the formula (IIc) are used especially in the form of acid addition salts, for example advantageously as benzoates.

For the manufacture of compounds of the formula (IIb) in which $R_a$ represents hyrogen, compounds of the formula

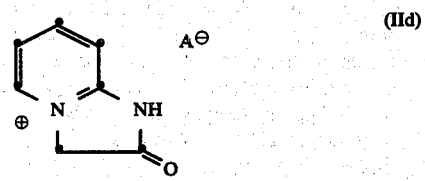

that are optionally substituted in the aromatic moiety and in which $A^\ominus$ represents the anion of an inorganic or organic acid are used as starting materials and are reacted with fumaric acid, maleic acid or maleic acid anhydride in the presence of a base, inorganic or organic bases being suitable. Inorganic bases are, for example, alkali metal hydroxides or hydrides, such as sodium or potassium hydroxide or sodium or potassium hydride. There are used as organic amines, for example, tertiary amines, such as trialkylamines, for example triethylamines or tri-n-butylamines, or cyclic amines, such as pyridine, picoline, quinoline or lutidine.

The free compounds initially obtainable by this method are converted by treatment with organic or inorganic acids into the compounds of the formula

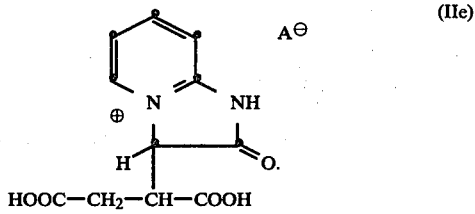

In the further course of the reaction, these compounds are reacted, optionally in the presence of one of the above-mentioned bases, with compounds of the formula $R_a$—CH=C ($R_b$)—CO—CH$_2$—$R_c$ (IIf) to form compounds of the formula

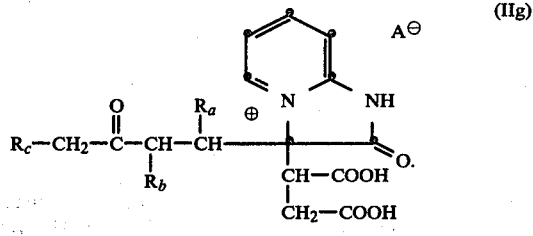

which are converted in the next reaction step by heating, for example at temperatures of between 80° and 160° C., with decarboxylation, into compounds of the formula

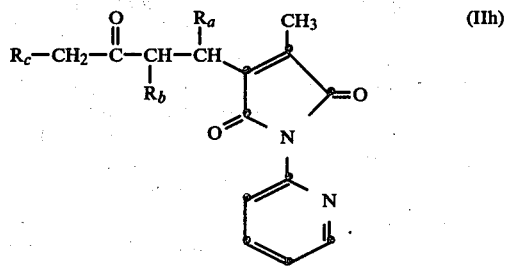

The thermal conversion of compounds of the formula (IIg) into compounds of the formula (IIh) is carried out, for example, in an optionally halogenated aromatic solvent, such as benzene, toluene, a xylene or chlorobenzene, or in a lower alkanecarboxylic acid, such as glacial acetic acid. The compounds of the formula (IIh) are then hydrolysed to form compounds of the formula (IIb). The hydrolysis is carried out, for example, in aqueous or aqueous-organic medium. Suitable organic solvents are especially highboiling polar solvents, such as ethers for example dioxane or tetrahydrofuran, N,N-dialkylamides, for example N,N-dimethylformamide of N,N-dimethylacetamide, or cyclic amides, such as N-methylpyrrolidone. The hydrolysis is carried out, for example, with the aid of an inorganic or organic acid, mineral acids, such as hydrohalic acids or sulphuric acid, being suitable as inorganic acids, and sulphonic acids, such as lower alkane- or optionally substituted benzene-sulphonic acids, such as methane- or p-toluene-sulphonic acid, or optionally substituted alkanecarboxylic acids, such as glacial acetic acid, being suitable as organic acids.

For the manufacture of compounds of formula (IIb) in which $R_a$ is other than hydrogen, compounds of the formula (IId) are used as starting materials and are reacted first with compounds of the formula (IIf) and then with fumaric acid, maleic acid or especially with maleic acid anhydride to form compounds of the formula (IIg) which, in turn, as described above, further react to form the corresponding compounds of the formula (IIb).

Re variant (b)

The starting materials of the formula (III) can be used in the form of salts, especially acid addition salts.

A group Y that can be converted into the group of the formula >CH($R_1$) can be converted, for example by reduction, into the group >CH($R_1$).

A compound of the formula III contains, for example, as the group Y that can be converted into >CH($R_1$), a group of the formula >C($R_1$)—COOH.

Such compounds are decarboxylated according to methods known per se to form compounds of the formula (I). The decarboxylation is generally carried out at elevated temperature, for example in a temperature range of approximately from 80° to 250° C., optionally in the presence of a catalytically active agent, for example a noble metal, such as copper powder, or an amine, such as an aromatic amine, for example aniline or quinoline, and optionally in an inert solvent. Suitable inert solvents are, for example, high-boiling optionally halogenated hydrocarbons, such as halogenated aromatic compounds, for example chlorobenzene.

For the manufacture of starting materials of the formula (III) in which Y represents a group of the formula >C($R_1$)—COOH, compounds of the formula

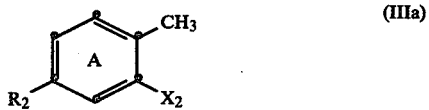

in which $X_2$ represents hydroxy or functionally modified hydroxy, or salts thereof, are used as starting materials and the methyl group is halogenated. For this purpose there is used, for example, N-halosuccinimide, such as the corresponding bromo- or chloro-derivative, sulphuryl chloride, bromine or chlorine, and the operation is preferably carried out in the presence of a radical-former, such as a peroxide, for example benzoyl peroxide, or an azo compound, for example azobisisobutyronitrile, or by the introduction of energy, such as irradiation, for example with UV light. The corresponding halogen is then exchanged for a cyano group by reaction with an alkali metal cyanide, such as sodium or potassium cyanide. The resulting acetonitrile is reacted with a dialkyl carbonate, such as diethyl carbonate, in the presence of an alkali metal, such as sodium, to form a compound of the formula

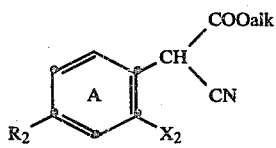

(IIIb)

in which alk represents an alkyl radical. In the next reaction step, it is possible, if desired, to introduce the radical $R_1$ by treatment with a corresponding halide or tosylate in the presence of a strong base, such as an alkali metal alkoxide, for example sodium methoxide, potassium methoxide or potassium tert.-butoxide, or an alkali metal amide or hydride, for example sodium amide or potassium hydride. The subsequent hydrolysis results in compounds of the formula

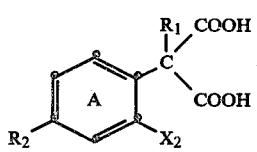

(IIIc)

which are cyclised in the presence of an acid, for example a protonic acid, such as a mineral acid, for example hydrohalic acid or sulphuric acid, such as alkane- or optionally substituted benzene-sulphonic acid, for example p-toluenesulphonic acid, or such as lower alkanecarboxylic acid, for example acetic acid, or a Lewis acid, such as a halide of elements of the third and fifth main groups and also the second and eighth sub-groups of the Periodic Table, for example aluminium(III) chloride or iron(III) chloride, to form corresponding compounds of the formula (III).

In a further preferred embodiment, it is possible to obtain compounds of the formula (III) in which Y represents the group $>C(R_1)$—COOH by using as starting material a compound of the formula (IIa) or a salt thereof in which $X_6$ represents a group of the formula $R_1$—$CH_2$—CO— and reacting this compound with ammonium polysulphide under pressure or with sulphur and a primary or secondary amine, advantageously with morpholine or thiomorpholine. In a resulting compound of the formula (II) in which $X_1$ represents a group of the formula —$CH(R_1)$—$X_3$, $R_1$ represents hydrogen and $X_3$ represents correspondingly substituted thiocarbamoyl or carbamoyl, or ammonium carboxylate, $X_3$ is converted by solvolysis, for example by hydrolysis, into carboxy.

In an optional additional reaction, compounds of the formula (IIa) in which $R_1$ is hydrogen can be converted into compounds of the formula (IIa) in which $R_1$ represents an aliphatic radical.

This is generally carried out by treatment with a reactive esterified aliphatic alcohol, such as a lower alkyl halide, in the presence of a strong base, such as an alkali metal alcoholate, for example sodium methoxide. In compounds of the formula (II) in which $X_2$ represents etherified hydroxy, the ether grouping is advantageously cleaved, for example by treatment with a strong acid, such as a hydrohalic acid, for example hydriodic acid, or with pyridine hydrochloride.

The resulting compounds of the formula

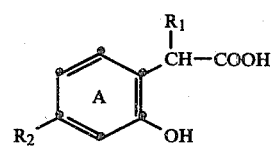

(IIIg)

are treated with pivalic acid chloromethyl ester in the presence of potassium iodide in dimethylformamide/acetone. From this there results a corresponding compound of the formula (III) in which Y represents a group of the formula $>C(R_1)$—COOH. The hydroxymethyl group can then be oxidised in the normal manner to form carboxy.

The group Y can also represent a group of the formula $>C=R'_1$ in which $R'_1$ represents a divalent aliphatic radical, for example alkylidene, especially lower alkylidene, a tautomeric form thereof, such as alkenylene, or alkenylidene, such as lower alkenylidene. Corresponding compounds of the formula (III) can be converted by reduction into compounds of the formula (I). The reduction can be carried out by catalytic hydrogenation with hydrogen, for example under a protective gas, such as nitrogen, and in the presence of a suitable hydrogenation catalyst, or by reaction with optionally complex hydrides, such as borane in tetrahydrofuran, or such as alkali metal borohydrides together with halides of elements of the third main group, for example with sodium borohydride and aluminum chloride or boron trifluoride in diglyme. Suitable hydrogenation catalysts are, for example, elements of the eighth sub-group or derivatives thereof, such as oxides or carbonates, which are optionally supported on a carrier, such as alkaline earth metal carbonates, for example barium carbonate, or active carbon. Examples of such catalysts are Raney-nickel, platinum oxide or palladium-on-carbon. Inert solvents are for example ethers, such as dioxane or tetrahydrofuran, or alcohols, such as lower alkanoles. The hydrogenation may be carried out for example in a temperature range of from approximately $-80°$ to approximately 200° C.

For the manufacture of starting materials of the formula (III) in which Y represents a group of the formula $>C=R'_1$, the procedure is according to methods known per se. Thus, for example, compounds of the formula (IIIc) are halogenated in the side chain $R_1$, for example using chlorine or bromine, N-chlorosuccinimide or N-bromosuccinimide, optionally in the presence of a radical-former, such as benzoyl peroxide or azobisisobutyronitrile. A $CO_2$ equivalent is then removed in customary manner by decarboxylation. In the next reaction step, dehydrohalogenation is carried out in the presence of a base, such as an alkali metal alkoxide, for example potassium tert.-butoxide, to form the corresponding compounds of the formula

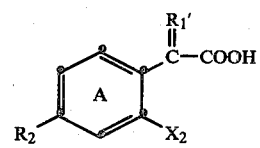

(IIId)

in which $X_2$ represents hydroxy or functionally modified hydroxy and which are cyclised, for example in the presence of an acid, for example a strong protonic or Lewis acid. Protonic acids are, for example, mineral acids, such as hydrohalic acids or sulphuric acid, alkane- or optionally substituted benzenesulphonic acids, for example p-toluenesulphonic acid, or alkanecarboxylic acids, such as glacial acetic acid. Suitable as Lewis acids are, for example, halides of boron, aluminium, tin, antimony or iron, such as boron trifluoride or aluminium chloride. The cyclisation is preferably carried out with hydriodic or hydrobromic acid and acetic anhydride or, if $X_2$ represents hydroxy, with a carbodiimide, such as dicyclohexyl carbodiimide.

Furthermore, for example, those groups Y in which Y represents a group of the formula $>C(R_1)$—$X_{11}$ and $X_{11}$ represents hydroxy, alkylthio, dialkylamino or diphenylsulphamoyl each phenyl moiety of which may optionally be substituted, or in which Y represents the carbonyl group, can be converted by reduction into the group of the formula $>CH(R_1)$.

Alkylthio $X_{11}$ is, for example, lower alkylthio, especially methyl- or ethyl-thio, and dialkylamino is, for example, di-lower alkylamino, especially dimethyl-amino. Each phenyl moiety of diphenylsulphamoyl may optionally be substituted by, for example, halogen or lower alkyl, and diphenylsulphamoyl may especially be di-(p-bromophenyl)-or di-(p-toluene)-sulphamoyl.

The reduction is carried out in a manner known per se. Thus, a suitable reducing agent is used and the operation is carried out under inert conditions, such as optionally under a protective gas, such as nitrogen, in an inert solvent or diluent, if necessary under pressure and/or while cooling or heating. Solvents are for example ethers, such as dioxane or tetrahydrofuran, or alcoholes, such as lower alkanols. The reaction is carried out for example in a temperature range of from approximately −80° to approximately 250° C.

There is used as reducing agent, for example, elemental hydrogen which is activated by a hydrogenation catalyst, also an optionally complex hydride or red phosphorus in the presence of hydrogen iodide or iodine. Suitable hydrogenation catalysts are, for example, elements of sub-group VIII of the Periodic Table or a derivative, for example a corresponding oxide, thereof. Such catalysts may be supported on a carrier, for example on active carbon, an alkaline earth metal carbonate or sulphate and also on a silica gel. Examples of such hydrogenation catalysts are, for example, platinum, platinum oxide or palladium, which are optionally supported on active carbon or barium sulphate, or Raney-nickel. Suitable as optionally complex hydrides are, for example, hydrides of elements of the first to third main groups or complex hydrides formed therefrom, such as diborane, aluminium hydride, lithium or sodium borohydride, lithium or sodium aluminium hydride, and also other complex hydrides, such as lithium triethyl borohydride.

In a preferred embodiment of the process, hydroxy, alkylthio, such as lower alkylthio, especially methylthio, and also dialkylamino, such as di-lower alkylamino, especially dimethylamino, are reduced by catalytically activated elemental hydrogen, palladium-on-carbon or Raney-nickel, for example, being used as the hydrogenation catalyst. The hydroxy group can also be replaced by hydrogen by using red phosphorus in the presence of hydriodic acid or iodine while heating, for example at from approximately 100° to approximately 250° C. In a further preferred method, the diphenylsulphamoyl group, each phenyl moiety of which may optionally be substituted, is reduced using a suitable optionally complex hydride, for example using an alkali metal borohydride, while heating, for example at from approximately 100° to approximately 200° C.

The carbonyl group Y is preferably reduced by a hydrazine in the presence of a base, such as an alkali metal hydroxide, analogously to the Wolff-Kishner reduction or the Huang-Minlon-variante respectively, or by a selective complex hydride, such as sodium cyanoborohydride in the presence of p-toluene-sulphonyl hydrazide, to form the group $>CH(R_1)$ in which $R_1$ represents hydrogen.

The starting compounds of the formula (III) in which Y represents the group of the formula $>C(R_1)$—OH can be obtained, for example, by reacting a compound of the formula

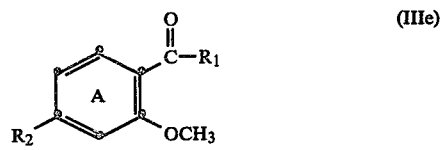

with hydrocyanic acid to form the corresponding cyanohydrin.

After hydrolysing the cyano group and cleaving ether, cyclisation is carried out, preferably in situ, in the presence of an acid or a dehydration agent to form the corresponding compound of the formula III.

Starting compounds of the formula (III) in which Y represents the group of the formula $>C(R_1)$—$X_{11}$ and $X_{11}$ represents alkylthio can be obtained by using a compound of the formula (IIIe) as starting material and treating it with a trihalomethane, such as chloroform, in the presence of a base, introducing the alkylthio group by reaction with an alkanethiol, then cleaving the ether with a suitable acid, for example a strong hydrohalic acid, and hydrolysing the trihalomethyl group with a base, such as an alkali metal hydroxide, to form the carboxy group. In the last step, the cyclisation catalyzed by an acid, such as protonic acid, takes place to form the corresponding compound of the formula (III).

Likewise using a compound of the formula (IIIe) as starting material, it is possible to obtain compounds of the formula (III) in which Y represents the group $>C(R_1)$—$X_{11}$ and $X_{11}$ optionally represents dialkylamino or diphenylsulphamoyl, each phenyl moiety of which may optionally be substituted. For this purpose, for example, a compound of the formula (IIIe) can be reacted with sodium cyanide and ammonium carbonate to form the hydantoin obtainable in this manner which can be hydrolysed using a base, such as an alkali metal hydroxide, to form the corresponding amino acid. The free amino group is then converted into the desired group $X_{11}$, for example by alkylation using an alkyl halide or by acylation using the corresponding sulphonyl halide. By simultaneously cleaving ether and cyclising, for example with hydrobromic acid and acetic anhydride, the desired starting compounds of the formula (III) can finally be obtained.

The starting material of the formula (III) in which Y represents carbonyl can be obtained, for example, by reacting a compound of the formula

with oxalyl chloride under cyclising conditions, such as in the presence of a strong acid.

Re variant (c):

The starting materials of the formula (IV) can be used in the form of their salts, especially acid addition salts.

A radical $X_5$ that can be converted into $R_2$ represents, for example, amino or a group of the formula —NH—$A_1$—$X_7$, in which $A_1$ represents a divalent hydrocarbon radical, such as lower alkylene, lower alkenylene, lower alkylene interrupted by aza, N-lower alkylaza, oxa or thia, or lower alkenylene interrupted by aza or N-lower alkylaza and $X_7$ represents hydroxy or reactive esterified hydroxy. Reactive esterified hydroxy $X_7$ is, for example, hydroxy esterified by an inorganic mineral acid, such as hydrohalic acid or sulphuric acid, by an organic sulphonic acid, such as lower alkane- or optionally substituted benzenesulphonic acid, for example methane- or p-toluenesulphonic acid, also by an organic carboxylic acid, such as lower alkanecarboxylic acid, for example acetic acid, and represents, especially, halogen, such as chlorine or bromine, or sulphonyloxy, such as p-toluenesulphonyloxy.

The conversion of —NH—$A_1$—$X_7$ into $R_2$ is carried out according to methods known per se. Thus, for example, the operation is carried out in the presence of a base, such as an alkali metal hydroxide or carbonate or an alkaline earth metal hydroxide or carbonate, for example sodium hydroxide or potassium bicarbonate, under inert conditions, such as under a protective gas, for example nitrogen, and/or in the presence or absence of an inert solvent in a temperature range of from approximately 0° to approximately 150° C. Solvents are for example ethers, such as dioxane, ketones, such as acetone, carboxylic acids, such as glacial acetic acid, or amides, such as dimethylformamide.

The radical $R_2$ can also be introduced directly by reacting compounds of the formula (IV) in which $X_5$ represents amino, or their salts, in the presence of a suitable base with compounds of the formula $X_7$—$A_1$—$X_7$. In this case it is also possible to form in situ compounds of the formula (IV) in which $X_5$ represents a group of the formula —NH—$A_1$—$X_7$ which further react, under the reaction conditions, directly to form corresponding compounds of the formula (I).

A radical $R_2$, if of non-aromatic nature, can be introduced directly, by reacting for example compounds of the formula (IV), in which $X_5$ is hydrogen, a radical containing a metal atom or optionally reactive esterified hydroxy, or a salt thereof with compounds of the formula $R_2$—$X_5'$ in which $X_5'$ denotes hydrogen, a radical containing a metal atom or optionally reactive esterified hydroxy or a salt thereof.

A radical containing a metal atom is for example an alkali metal atom, such as lithium or sodium. Reactive esterified hydroxy is for example hydroxy esterified by a mineral acid, such as hydrohalic acid, or by a sulfonic acid, such as an optionally substituted benzenesulphonic acid.

First and foremost, for example compounds of the formula (IV) are reacted with compounds of the formula $R_2$—$X_5'$ in which one of the radicals $X_5$ and $X_5'$ denotes an alkali metal atom, such as lithium, and the other is halogen, such as bromine.

In case $X_5$ is hydrogen and $X_5'$ is hydroxy or halogen, the reaction is carried out in presence of a lewis acid. If $X_5$ denotes halogen and $X_5'$ is hydrogen, the reaction will be carried out in presence of a condensating agent.

For the manufacture of starting materials of the formula (IV) the starting materials used are, for example, compounds of the formula

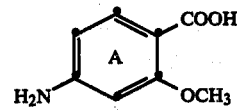

or salts thereof, which are reacted, for example, with a benzyl halide, such as benzyl chloride, in the presence of a base, such as an alkali metal hydroxide, for example sodium hydroxide, and then with dilute acid. The resulting 4-N,N-dibenzylamino-2-methoxybenzoic acid is converted into the corresponding acid chloride using thionyl chloride. In the next reaction step, reaction is carried out with diazomethane, to obtain a compound of the formula

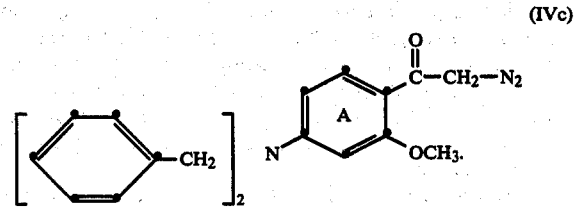

The compound of the formula (IVc) is then solvolysed in the presence of silver or silver oxide or by UV irradiation, hydrolysis resulting in the compound of the formula

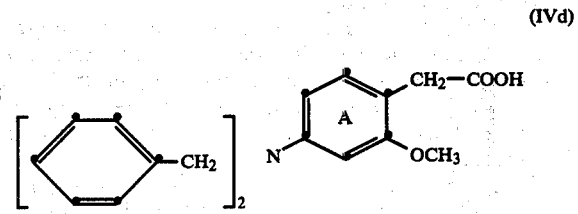

or its salt and alcoholysis resulting in the corresponding ester of the compound (IVd).

If desired, the radical $R_1$, $R_1$ being other than hydrogen, can be introduced into compounds of the formula (IVd), for example by treatment with a reactive esterified aliphatic alcohol. The two benzyl groups are then removed, for example by catalytic hydrogenation. The resulting reaction product is cyclised, for example using 48% hydrobromic acid and acetic anhydride, to form the compound of the formula

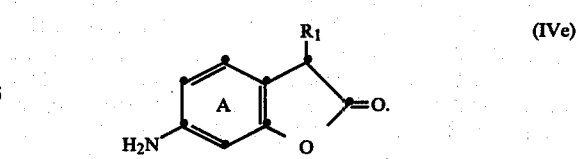

By reaction with a compound of the formula $X_7-A_1-X_7$ in the presence of a base, the amino group can be converted into the group $X_5$.

Compounds of the formula (I) in which $R_2$ represents pyrrol-1-yl can be obtained by reacting compounds of the formula (IV) in which $X_5$ represents amino, or their salts, with 2-butene-1,4-diol or a reactively esterified derivative thereof, in the presence of a protonic acid, such as a lower alkanecarboxylic acid, to pyrrolidin-1-yl, dehydrogenating it in the presence of a catalyst, such as palladium, or in the presence of a dehydrogenating catalyst, such as a quinone, for example 2,3-dichloro-5,6-dicyano-p-benzoquinone or tetrachloro-p-benzoquinone, or a selenium derivative, such as selenium dioxide, or an element of the sub-group VIII, such as palladium, or by treating compounds of the formula (IVe) or their salts with a 2,5-di-lower alkoxytetrahydrofuran, such as 2,5-dimethoxytetrahydrofuran, for example while heating.

Furthermore, the pyrrole ring $R_2$ can be synthesised, for example by reacting the amino group in compounds of the formula (IVe) wherein $X_5$ is amino with an optionally reactively esterified derivative of 1,3-butadiene-1,4-diol, for example with 1,4-dibromo-1,3-butadiene, if necessary while heating and under protective gas, for example nitrogen, and in an inert solvent or diluent.

It is also possible to synthesise the pyrrole ring $R_2$ in a manner analogous to that described by Knorr-Paal by treating the amino group in compounds of the formula (IVe) with optionally acetalised 1,4-dioxobutane, it being possible to operate under inert conditions, for example under protective gas and while heating and in an inert solvent.

A further process variant for synthesising the pyrrole ring $R_2$ consists, for example, in reacting compounds of the formula (IV) in which $X_5$ represents, for example, the group of the formula $-NH-CH=CH-CH=CH-OH$ or a reactive esterified form or an optionally acetalised tautomeric form thereof. In this case the reaction is advantageously carried out under inert conditions and while heating.

In this context, reactive esterified hydroxy is in each case hydroxy esterified, for example, by a mineral acid, such as hydrohalic acid, for example hydrobromic acid, or by a sulphonic acid, such as lower alkane- or optionally substituted benzene-sulphonic acid, or p-toluenesulphonic acid.

Likewise, amines $R_2-H$, sufficiently nucleophile, can be introduced directly into compounds of the formula (IV), in which $X_5$ denotes a radical replaceable by the radical $R_2$. In case $X_5$ denotes for example halogen, preferable chlorine, bromine or iodine, the reaction can be carried out in the presence or absence of a solvent and, according to the choice of halogen, at low temperature up to the boiling point of the corresponding solvent. Preferably, in the position adjacent to $X_5$ a substituent is located having a strong $-I-$ or $-M-$effect, such as nitro, halogen or trifluoromethyl. Sometimes it will be advantageous carrying out the reaction under pressure or at elevated temperature. Preferably, the amines are used in excess. In case compounds of the formula (IV) in which $X_5$ is hydrogen, are used, they are first of all treated with an oxidizing agent, such as lead tetracetate, for example in presence of a suitable acid, such as glacial acetic acid, and at room temperature and are subsequently reacted with a the corresponding amine $R_2-H$ in an inert solvent, such as an ether, for example dioxane, under warming, for example at the refluxing temperature of the corresponding solvent.

Re variant (d):

The starting materials of the formula (V) can be used in the form of their salts, especially in the form of acid addition salts.

A group Z that can be converted into the carbonyl group is, for example, the methylene group or represents a radical that can be hydrolysed to form the carbonyl group.

The methylene group can be converted into the carbonyl group, for example by oxidation. The oxidation is carried out in a manner known per se, for example using a suitable oxidising agent, under inert conditions, for example in an inert solvent or diluent and while cooling or heating.

Suitable as oxidising agents are, for example, oxides of elements of the sub-group VIII of the Periodic Table, such as osmium tetroxide or, especially, ruthenium tetroxide, and also hypochlorites, such as alkali metal or alkaline earth metal hypochlorites, for example sodium or calcium hypochlorite.

Inert solvents or diluting agents are, for example, lower alkanecarboxylic acids, such as acetic acid, ketones, such as acetone, ethers, such as dioxane or tetrahydrofuran, amides, such as dimethylformamide, or mixtures thereof.

Suitable as groups that can be converted by hydrolysis into the carbonyl group are, for example, thiocarbonyl or optionally N-substituted iminomethylene. As substituents of imino there may be mentioned, for example, an optionally substituted hydrocarbon radical, such as an aliphatic or aromatic radical, for example lower alkyl or optionally substituted phenyl, or an acyl group derived from a carboxylic acid or a semiester of carbonic acid, such as lower alkanoyl or optionally substituted benzoyl, or optionally substituted alkoxycarbonyl, such as lower alkoxycarbonyl.

The hydrolysis is carried out, for example, in the presence or absence of a solvent or diluent, if necessary while cooling or heating and/or under inert gas, for example nitrogen. Inert solvents or diluting agents are, for example, lower alkanecarboxylic acids, such as acetic acid, ketones, such as acetone, ethers, such as dioxane or tetrahydrofuran, amides, such as dimethylformamide, or mixtures thereof.

The starting material of the formula (V) in which Z represents methylene can be obtained, for example, by etherifying a compound of the formula

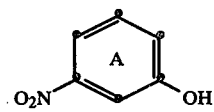

(Va)

with a compound of the formula $R_1-CO-CH_2-Cl$ (Vb) and cyclising this ether with titanium(III) chloride in a lower alkanol to form the compound of the formula

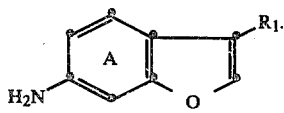
(Vc)

After converting the free amino group into $R_2$, for example by customary alkylation, the double bond of the benzofuran in question is hydrogenated by reduction, for example using an optionally complex hydride, especially using potassium borohydride, to form the corresponding compound of the formula (V).

The starting material of the formula (V) in which Z represents thiocarbonyl can be obtained, for example, by using as starting materials, for example, compounds of the formula (IIa) or salts thereof in which $X_6$ represents a group of the formula $R_1$—$CH_2$—$CO$— and reacting these with ammonium polysulphide under pressure or with sulphur and a primary or secondary amine, advantageously with morpholine or thiomorpholine. In a resulting compound of the formula (II) in which $X_1$ represents a group of the formula —$CH(R_1)$—$X_3$, $R_1$ represents hydrogen and $X_3$ represents correspondingly substituted thiocarbamoyl or carbamoyl, or ammonium carboxylate, $X_3$ is converted by solvolysis, for example by hydrolysis, into carboxy. In an optional additional reaction, compounds of the formula (IIa) in which $X_6$ is a group of the formula $R_1$—$CH_2$—$CO$ and $R_1$ is hydrogen, can be converted into compounds of the formula (IIa) in which $X_6$ is a group of the formula $R_1$—$CH_2$—$CO$ and $R_1$ represents an aliphatic radical. This is generally carried out by treatment with a reactive esterified aliphatic alcohol, such as a lower alkyl halide, in the presence of a strong base, such as an alkali metal alcoholate, for example sodium methoxide. In resulting compounds of the formula (II) in which $X_2$ represents etherified hydroxy, the ether grouping is advantageously cleaved, for example by treatment with a strong acid, such as a hydrohalic acid, for example hydriodic acid, or with pyridine hydrochloride. In resulting compounds of the formula (IIIg), the carboxy groups are converted into the dithiocarboxy groups, for example via an ester with a thiol with subsequent treatment with phosphorus pentasulphide. In the last step, cyclisation can be carried out to form the corresponding compound of the formula (V).

Re variant (e):

The starting compounds of the formula (VI) may be in the form of their salts, especially in the form of acid addition salts.

A ring A' that can be converted into the ring A contains, for example, the substitution pattern of the ring A and two double bonds and, in addition, at two carbon atoms, one hydrogen atom in each case. Accordingly, conversion into the ring A can be carried out by dehydrogenation.

Dehydrogenation is carried out in a manner known per se. A suitable dehydrogenation agent is used and the operation is carried out, if necessary, while heating, for example in a temperature range of from approximately 100° to approximately 300° C., in an inert solvent or diluent, optionally under a protective gas, such as nitrogen, and/or, if necessary, under pressure.

There come into consideration as dehydrogenation agents, for example, elements of the sub-groups, preferably those of the sub-group VIII of the Periodic Table, such as palladium or platinum, or corresponding salts, such as ruthenium triphenyl phosphide chloride; the agents may be supported on suitable carriers, such as aluminium oxide or a silica. Further preferred dehydrogenation agents are, for example, quinones, such as p-benzoquinones, for example tetrachloro-p-benzoquinone or 2,3-dichloro-5,6-dicyano-p-benzoquinone, or such as anthraquinones, for example phenanthrene-9,10-quinone. It is also possible to use N-halosuccinimides, such as N-chlorosuccinimide, manganese compounds, such as barium manganate or manganese dioxide, and selenium derivatives, such as selenium dioxide or diphenylselenium bis-trifluoroacetate.

The starting material of the formula (VI) in which $R_1$ represents methyl can be obtained, for example, by using a compound of the formula (IIb) as the starting material and reacting it with an acid addition salt of a compound of the formula $R_2$—H.

A compound of the formula (I) obtainable according to the invention can be converted in a manner known per se into a different compound of the formula (I).

A hydrogen atom as substituent of an aromatic ring system can be replaced in a manner known per se in the presence of a halogenating agent by a halogen atom.

For example the replacement of hydrogen by bromine can be effected for example by elementary bromine according to "Methoden der Organischen Chemie," Houben-Weyl, Vol. 5/4, pp. 233–249, in an inert solvent. Furthermore, the bromination can be effected by the following bromating agents: hypobromous acid, acylhypobromides or further organic bromine compounds, for example N-bromosuccinimide, N-bromoacetamide, N-bromophthalimide, pyridinium perbromide, dioxane dibromide, 1,3-dibromo-5,5-dimethyl-hydantoin and 2,4,4,6-tetrabromo-2,5-cyclohexadien-1-one.

The corresponding chlorination can be effected according to Houben-Weyl (4. Edition), Vol. 5/3, pp. 651–673, for example, preferably with elementary chlorine, for example in a halogenated hydrocarbon, such as chloroform, and under cooling, for example at approximately $-10°$ to approximately $+10°$ C.

The replacement of hydrogen by iodine can be effected by elementary iodine in the presence of mercury oxide or nitric acid. Instead of using elementary iodine, it is possible to use for example also potassium iodide in the presence of a thallium salt, for example thallium (III)-trifluoroacetate according to Tetrahedron Letters (1969), p. 2427.

It is also possible to alkylate the benzo moiety of the ring system, for example with a lower alkanol or a lower alkyl halide or a phosphoric acid lower alkyl ester in the presence of Lewis acids (Friedel-Crafts-alkylation). In a compound of the formula (I) in which the aromatic ring A contains bromine, it is possible, for example, to replace the bromine by lower alkyl by reaction with a lower alkyl bromide in the presence of an alkali metal.

A hydrogen atom in an aromatic ring can be replaced by an acyl group in a manner known per se. For example, the introduction of the acyl group can be effected analogous to the Friedel-Crafts-acylation (cf. G. A. Olah, Friedel-Crafts and Related Reactions, Vol. I, Interscience, New York, 1963–1965), for example by reaction with a reactive functional derivative, especially a halide or an anhydride, or an organic carboxylic acid in the presence of a Lewis acid, for example aluminium chloride, antimony (III)-chloride or antimony (V) chloride, iron (III)-chloride, zinc (II)-chloride or boron trifluoride.

If the aromatic ring A contains hydroxy as substituent, then the hydroxy can be etherified in a manner known per se. The reaction with an alcohol component, for example with a lower alkanol, such as ethanol, in the presence of acids, for example mineral acid, such as sulphuric acid, or in the presence of dehydrating agents, such as dicyclohexyl carbodiimide, results in lower alkoxy. Conversely, ethers can be cleaved into phenols by treatment with acids, such as mineral acids, for example hydrohalic acid, such as hydrobromic acid, or such as Lewis acids, for example halides of elements of the third main group, such as boron tribromide, or by treatment with pyridine hydrochloride or thiophenol.

Furthermore, hydroxy can be converted into lower alkanoyloxy, for example by reaction with a desired lower alkanecarboxylic acid, such as acetic acid, or a reactive derivative thereof, for example in the presence of an acid, such as a protonic acid, for example hydrochloric acid, hydrobromic acid, sulphuric acid, phosphoric acid, or a benzenesulphonic acid, in the presence of a Lewis acid, for example boron trifluoride etherate, or in the presence of a water-binding agent, such as dicyclohexyl carbodiimide. Conversely, esterified hydroxy can be solvolysed, for example by base catalysis, to form hydroxy.

If the ring A is substituted by lower alkylthio, the latter can be oxidised in customary manner to form the corresponding lower alkane-sulphinyl or -sulphonyl. There come into consideration as suitable oxidising agents for the oxidation to the sulphoxide stage, for example, inorganic peracids, such as peracids of mineral acids, for example periodic acid or persulphuric acid, organic peracids, such as corresponding percarboxylic or persulphonic acids, for example performic, peracetic, trifluoroperacetic or perbenzoic acid or p-tolueneper-sulphonic acid, or mixtures of hydrogen peroxide and acids, for example a mixture of hydrogen peroxide and acetic acid.

The oxidation is often carried out in the presence of suitable catalysts; there may be mentioned as catalysts suitable acids, such as optionally substituted carboxylic acids, for example acetic acid or trifluoroacetic acid, or transition metal oxides, such as oxides of elements of sub-group VII, for example vanadium, molybdenum or tungsten oxide. The oxidation is carried out under mild conditions, for example at temperatures of from approximately $-50°$ to approximately $+100°$ C.

The oxidation to the sulphone stage can also be carried out correspondingly with dinitrogen tetroxide as the catalyst in the presence of oxygen at low temperatures, as can the direct oxidation of the lower alkylthio to form the lower alkanesulphonyl. In this case, however, the oxidising agent is normally used in excess.

If the ring A of the formula I is substituted by lower alkyl-sulphinyl or -sulphonyl, it is possible to reduce this according to methods known per se to form the corresponding lower alkylthio compound, and, when using lower alkanesulphonyl derivatives as starting materials, also to form lower alkanesulphinyl. Suitable as reducing agents are, for example, catalytically activated hydrogen, there being used noble metals or oxides, such as palladium, platinum or rhodium or their oxides, optionally supported on a suitable carrier, such as active carbon or barium sulphate. Also suitable are reducing metal cations, such as tin(II), lead(II), copper(I), manganese(II), titanium(II), vanadium(II), molybdenum(III) or tungsten(III) compounds, hydrogen halides, such as hydrogen chloride, bromide or iodide, hydrides, such as complex metal hydrides, for example lithium aluminium hydride, sodium borohydride, tributyltin hydride, phosphorus compounds, such as phosphorus halides, for example phosphorus trichloride, phosphorus tribromide, phosphorus pentachloride or phosphorus oxychloride, phosphines, such as triphenylphosphine, or phosphorus pentasulphide pyridine, or sulphur compounds, such as mercaptans, thio acids, such as thiophosphoric acids or dithiocarboxylic acids, dithionite or sulphur/oxygen complexes, such as an iodine/pyridine/sulphur dioxide complex.

Compounds of the formula (I) containing unsaturated radicals, such as lower alkenyl or lower alkenylen, can be converted in a matter known per se into corresponding compounds containing saturated radicals. For example, the hydrogenation can be effected by catalytic hydrogenahydrogenation in the presence of hydrogenating catalysts, which are for example precious metals or a derivative thereof, such as an oxide thereof, such as Nickel, Raney-Nickel, Palladium, Platinum oxide, which agents may be supposed on suitable carriers, such as carbon or calcium carbonate. The hydrogenation can be effected preferably at a pressure between 1 and approximately 100 at and at temperatures between approximately $-80°$ to approximately $200°$ C., more especially between room temperature and approximately $100°$ C. The reaction is carried out practically in a solvent, such as in water, in a lower alkanol, for example ethanol, isopropanol or n-butanol, in an ether, for example dioxane, or in a lower alkanecarboxylic acid, for example acetic acid.

Conversely, in cyclic systems $R_2$ one or more multiple bonds can be introduced. For this, suitable dehydrogenating agents can be used, for example elements of the subgroups, preferable of subgroup VIII of the Periodic Table, for example Palladium or platinium, or derivatives of precious metals, for example quinones, such as p-benzoquinones, for example tetrachloro-p-benzoquinone or 2,3-dichloro-5,6-dicyano-p-benzoquinone, or anthraquinones, such as phenanthren-9,10-quinone. Furthermore, N-halogeno-succinimides, such as N-chlorosuccinimide, manganese compounds, such as barium manganate or man manganese dioxide, and selenium derivatives, such as selenium dioxide or diphenylsleneium-bis-trifluoroacetate, can be used.

Salts of compounds of the formula (I) can be manufactured in a manner known per se. Thus, for example, acid addition salts of compounds of the formula (I) are obtained by treatment with an acid or a suitable ion exchange reagent. Salts can be converted in customary manner into the free compounds; for example, acid addition salts can be converted by treatment with a suitable basic agent.

As a result of the close relationship between the novel compounds in free form and in the form of their salts, hereinbefore and hereinafter the free compounds or their salts shall be understood to mean optionally also the corresponding salts or free compounds, respectively, where appropriate with regard to meaning and purpose.

The novel compounds, including their salts, can also be obtained in the form of their hydrates, or include other solvents used for the crystallisation.

Depending upon the starting materials and methods chosen, the novel compounds may be in the form of one of the possible isomers or in the form of mixtures thereof, for example, depending on the number of asymmetric carbon atoms, in the form of pure optical isomers, such as antipodes, or in the form of mixtures of isomers, such as racemates, mixtures of diastereoisomers or mixtures of racemates.

Resulting mixtures of diastereoisomers and mixtures of racemates can be separated on the basis of the physico-chemical differences between the constituents, in known manner, into the pure isomers, diastereoisomers or racemates, for example by chromatography and/or fractional crystallisation. Resulting racemates can furthermore be resolved into the optical antipodes by known methods, for example by recrystallisation from an optically active solvent, with the aid of microorganisms or by converting into diastereoisomeric salts or esters, for example by reacting an acidic end product with an optically active base that forms salts with the racemic acid, or with an optically active carboxylic acid or a reactive derivative thereof, and separating the mixture of diastereoisomers obtained in this manner, for example on the basis of their different solubilities, into the diastereoisomers, from which the desired enantiomer can be freed by the action of suitable agents. Advantageously, the more active enantiomer is isolated.

The invention relates also to those embodiments of the process according to which compounds obtainable as intermediates at any stage of the process are used as starting materials and the remaining steps are carried out or a starting material is used in the form of a salt or, especially, is formed under the reaction conditions.

In the process of the present invention it is preferable to use those starting materials which result in the compounds described at the beginning as being especially valuable. The invention relates also to novel starting materials, their use, for example as the active ingredients of medicaments, to formulation processes and to processes for their manufacture.

The pharmaceutical preparations according to the invention, which contain the compound according to the invention or pharmaceutically acceptable salts thereof, are for topical application, and also for enteral, such as oral or rectal, and parenteral administration to (a) warm-blooded animal(s) and contain the pharmacological active ingredient alone or together with a pharmaceutically acceptable carrier. The daily dosage of the active ingredient depends on age and the individual condition, and on the method of administration.

The novel pharmaceutical preparations contain, for example, from approximately 10% to approximately 80%, preferably from approximately 20% to approximately 60%, of active ingredient. Pharmaceutical preparations according to the invention for enteral or parenteral administration are, for example, those in dosage unit forms, such as dragées, tablets, capsules or suppositories, and also ampoules. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée cores.

Suitable carriers are especially fillers, such as sugar, for example lactose, saccharose, mannitol or sorbitol, cellulose preparations and/or calcium phosphates, for example tricalcium phosphate or calcium biphosphate, also binders, such as starch pastes using, for example, corn, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that are optionally resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragée coatings, for example for identification purposes or to indicate different doses of active ingredient.

Further pharmaceutical preparations for oral administration are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material; as base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain substances which increase the viscosity, for example sodium carboxymethylcellulose, sorbitol and/or dextran, and, optionally, also stabilisers.

There come into consideration as pharmaceutical preparations for topical use especially creams, ointments, pastes, foams, tinctures and solutions that contain from approximately 0.1% to approximately 5% of active ingredient.

Creams are oil-in-water emulsions that contain more than 50% of water. As oily base there are used especially fatty alcohols, for example lauryl, cetyl or stearyl alcohol, fatty acids, for example palmitic or stearic acid, liquid to solid waxes, for example isopropyl myristate, wool waxes or beeswax, and/or hydrocarbons, for example petroleum jelly (petrolatum) or paraffin oil. As emulsifiers there come into consideration surface-active substances having predominantly hydrophilic properties, such as corresponding non-ionic emulsifiers, for example fatty acid esters of polyalcohols, or ethylene oxide adducts thereof, such as polyglycerine fatty acid esters or polyoxyethylene sorbitan fatty acid esters (Tweens), also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the aqueous phase are, inter alia, agents that reduce the drying out of the creams, for example polyalcohols, such as glycerine, sorbitol, propylene glycol and/or polyethylene glycols, also preservatives, perfumes etc.

Ointments are water-in-oil emulsions that contain up to 70%, but preferably from approximately 20% to approximately 50%, of water or aqueous phases. As fatty phase there come into consideration especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool waxes. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerine, propylene glycol, sorbitol and/or polyethylene glycol, and also preservatives, perfumes etc.

Fatty ointments are anhydrous and contain as base especially hydrocarbons, for example paraffin, petroleum jelly and/or liquid paraffins, and also natural or partially synthetic fats, for example coconut fatty acid triglyceride, or preferably hardened oils, for example hydrogenated ground nut oil or castor oil, and also fatty acid partial esters of glycerine, for example glycerine mono- and di-stearate, and also, for example, the fatty alcohols, which increase the water-absorbing capacity, emulsifiers and/or additives mentioned in connection with the ointments.

Pastes are creams and ointments containing powder ingredients that absorb secretions, such as metal oxides, for example titanium oxide or zinc oxide, also talc and/or aluminium silicates, the purpose of which is to bind any moisture or secretions present.

Foams are administered, for example, from pressurised containers and are liquid oil-in-water emulsions in aerosol form, halogenated hydrocarbons, such as chlorofluoro-lower alkanes, for example dichlorodifluoromethane and dichlorotetrafluoroethane, being used as propellants. For the oily phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers having predominantly hydrophilic properties, such as polyoxyethylene sorbitan fatty acid esters (Tweens), and those having predominantly lipophilic properties, such as sorbitan fatty acid esters (Spans). In addition, there may be used customary additives, such as preservatives etc.

Tinctures and solutions generally have an aqueous ethanolic base to which there are added, inter alia, polyalcohols, for example glycerine, glycols, and/or polyethylene glycol, as humectants for reducing evaporation, and fat-restoring substances, such as fatty acid esters with lower polyethylene glycols, that is to say lipophilic substances that are soluble in the aqueous mixture, to replace the fatty substances that are taken from the skin by the ethanol, and, if necessary, other adjuncts and additives.

The pharmaceutical preparations for topical application are manufactured in a manner known per se, for example by dissolving or suspending the active ingredient in the base or, if necessary, in a part thereof. When processing the active ingredient in the form of a solution, it is usually dissolved in one of the two phases before emulsification; when processing the active ingredient in the form of a suspension, it is mixed with a part of the base after emulsification and then added to the remainder of the formulation.

The dosage of the active ingredient depends on the species of warm-blooded animal, age and individual condition, and on the method of administration. In normal cases, the estimated approximate daily dose in the case of oral administration to a warm-blooded animal weighing approximately 75 kg is from approximately 100 to approximately 600 mg, advantageously divided into several equal partial doses.

The following Examples illustrate the invention described above but are not intended to limit the scope of the invention in any way. Temperatures are given in degrees Centigrade.

EXAMPLE 1

A mixture of 18.2 g (0.1 mole) of 4-methyl-3-(3-oxobutyl)-maleic acid anhydride and 22 g (0.105 mole) of morpholinium benzoate in 400 ml of benzene is heated under reflux for 48 hours using a water separator. The benzene is removed in vacuo, the residue is taken up in methylene chloride and the organic phase is extracted twice with saturated sodium bicarbonate solution. The crude product remaining after drying and after removal of the methylene chloride is chromatographed over silica gel with petroleum ether/ether. Pale-yellow crystals are obtained, which are recrystallised from methylene chloride/ether. In this manner 3-methyl-6-morpholino-benzofuran-2(3H)-one having a melting point of 118°–121° C. is obtained.

The starting material can be manufactured as follows:
A hot solution of 80 g (2 moles) of sodium hydroxide in 200 ml of water is added in portions, while stirring, to a mixture of 341 g (2 moles) of the hydrochloride of imidazo[1,2-a]pyridin-2(3H)-one in 700 ml of water. Then, a solution of 250.7 g (2.16 moles) of maleic acid in 600 ml of water is added dropwise in such a manner that the internal temperature of the reaction mixture remains between 40° and 45° C. After 30 hours at room temperature (20°–25° C.) the mixture is cooled to 5° C., the resulting precipitate is filtered off, the filtrate is concentrated in vacuo to approximately half its volume, and the resulting product is filtered with suction. The combined residues are washed with a little cold methanol and dried in vacuo at 50° C. 400 g of 3-(1,2-dicarboxyethyl)-imidazo[1,2-a]pyridin-2(3H)-one having a melting point of 193° (decomposition) are obtained. The resulting product is stirred at room temperature for 6 hours with 650 ml of concentrated hydrochlorid acid. After cooling to 5° C., the precipitate is filtered off, the filtrate is concentrated in vacuo to approximately half its volume and the resulting product is filtered with suction. The combined residues are washed with acetone and dried in vacuo at 50° C. In this manner the hydrochloride of 3-(1,2-dicarboxyethyl)-imidazo[1,2-a]pyridin-2(3H)-one having a melting point of 205° C. (decomposition) is obtained.

A mixture of 114.7 g (0.4 mole) of the hydrochloride of 3-(1,2-dicarboxyethyl)-imidazo[1,2-a]pyridin-2(3H)-one, 36.4 (0.52 mole) of methyl vinyl ketone, 150 ml of methanol and 150 ml of water is stirred at room temperature for 36 hours and then concentrated to dryness by evaporation in vacuo at approximately 45° C. The resulting crude product is taken up in 300 ml of glacial acetic acid, 15 g of sodium acetate are added and the whole is boiled under reflux until $CO_2$ evolution is complete. The solvent is then removed in vacuo, a mixture of 150 ml of 6 M sulphuric acid and 150 ml of tetrahydrofuran is added to the residue and the whole is maintained at 50° C. for 8 hours. After removing the tetrahydrofuran in vacuo, the reaction mixture is diluted with water, extracted with methylene chloride and filtered through silica gel. Distillation of the crude product in a high vacuum (115°–125° C./8 Pa) yields 4-methyl-3-(3-oxobutyl)-maleic acid anhydride as a spectroscopically homogeneous pale-yellow oil.

EXAMPLE 2

A mixture of 18.2 g (0.1 mole) of 4-methyl-3-(3-oxobutyl)-maleic acid anhydride and 20.3 g (0.105 mole) of pyrrolidinium benzoate in 400 ml of benzene is heated under reflux for 24 hours using a water separator. The benzene is then removed in vacuo and the residue that remains is partitioned between methylene chloride and saturated sodium bicarbonate solution. The crude product remaining after drying and after removal of the methylene chloride is chromatographed over silica gel with petroleum ether/ether. Subsequent recrystallisation from ether. Subsequent recrystallisation from ether/petroleum ether yields 3-methyl-6-(pyrrolidin-1-yl)-benzofuran-2(3H)-one having a melting point of 101°–103° C.

EXAMPLE 3

A mixture of 9.1 g (0.05 mole) of 4-methyl-3-(3-oxobutyl)-maleic acid anhydride and 11 g (0.053 mole) of piperidinium benzoate in 200 ml of benzene is heated under reflux for 48 hours using a water separator. The benzene is removed in vacuo and the residue that remains is partitioned between methylene chloride and saturated sodium bicarbonate solution. The crude product remaining after drying and after removal of the methylene chloride is chromatographed over silica gel with petroleum ether/ether. Subsequent recrystallisation from ether/petroleum ether yields 3-methyl-6-(piperidin-1-yl)-benzofuran-2(3H)-one having a melting point of 78°–80° C.

EXAMPLE 4

A mixture of 18.2 g (0.1 mole) of 4-methyl-3-(3-oxobutyl)-maleic acid anhydride and 23.2 g (0.105 mole) of hexahydroazepinium benzoate in 400 ml of benzene is heated under reflux for 48 hours using a water separator. The benzene is removed in vacuo and the residue remaining is partitioned between methylene chloride and saturated sodium bicarbonate solution. The crude product remaining after drying and after removal of the methylene chloride is chromatographed over silica gel with petroleum ether/ether. Subsequent recrystallisation from ether/petroleum ether yields 6-(hexahydroazepin-1-yl)-3-methylbenzofuran-2(3H)-one having a melting point of 57°–59° C.

EXAMPLE 5

A mixture of 19.6 g (0.1 mole) of 4-methyl-3-(2-methyl-3-oxobutyl)-maleic acid anhydride and 21.3 g (0.11 mole) of pyrrolidinium benzoate in 400 ml of benzene is heated under reflux for 30 hours using a water separator. The benzene is removed in vacuo and the residue is partitioned between ether and saturated sodium bicarbonate solution. The crude product remaining after drying and concentrating by evaporation the organic phase is chromatographed over silica gel. Elution with petroleum ether/ether and subsequent recrystallisation of the pure fractions from ether/petroleum ether yields, 3,5-dimethyl-6-(pyrrolidin-1-yl)-benzofuran-2(3H)-one having a melting point of 67°–69° C.

The starting material can be manufactured as follows:

A mixture of 172 g (0.6 mole) of the hydrochloride of 3-(1,2-dicarboxyethyl)-imidazo[1,2-a]pyridin-2(3H)-one, 65.5 g (0.78 mole) of 3-methyl-3-buten-2-one, 220 ml of methanol and 220 ml of water is stirred at room temperature for 36 hours and then concentrated to dryness by evaporation in vacuo at approximately 45° C. The resulting crude product is taken up in 400 ml of glacial acetic acid, 22.5 g of sodium acetate are added and the mixture is boiled under reflux until $CO_2$ evolution is complete. Then, the solvent is removed in vacuo, a mixture of 225 ml of 6 M sulphuric acid and 225 ml of tetrahydrofuran is added to the residue and the whole is heated under reflux for 8 hours. After removing tetrahydrofuran in vacuo, the reaction mixture is diluted with water and extracted with methylene chloride. The crude product remaining after drying and concentrating by evaporation the organic phase is chromatographed over silica gel with petroleum ether/ether. The subsequent distillation (100° C./8.10$^{-8}$ torr) yields 4-methyl-3-(2-methyl-3-oxobutyl)-maleic acid anhydride in the form of a pale-yellow oil.

EXAMPLE 6

A mixture of 19.6 g (0.1 mole) of 4-methyl-3-(2-methyl-3-oxobutyl)-maleic acid anhydride and 23 g (0.11 mole) of morpholinium benzoate in 400 ml of benzene is heated under reflux for 60 hours using a water separator. The benzene is removed in vacuo and the residue is partitioned between methylene chloride and saturated sodium bicarbonate solution. The crude product remaining after drying and concentrating by evaporation the organic phase is chromatographed over silica gel. Elution with petroleum ether/ether and subsequent recrystallisation of the pure fractions from ether/petroleum ether yields 3,5-dimethyl-6-morpholinobenzofuran-2(3H)-one having a melting point of 108°–109° C.

EXAMPLE 7

A mixture of 19.6 g (0.1 mole) of 4-methyl-3-(1-methyl-3-oxobutyl)-maleic acid anhydride and 23 g (0.11 mole) of morpholinium benzoate in 400 ml of benzene is heated under reflux for 44 hours using a water separator. The benzene is removed in vacuo, the residue is taken up in methylene chloride and the organic phase is extracted twice with saturated sodium bicarbonate solution. The crude product remaining after drying and after removal of the methylene chloride is chromatographed over silica gel with petroleum ether/ether.

There is obtained in this manner, after recrystallisation from ether/petroleum ether, 3,4-dimethyl-6-morpholinobenzofuran-2(3H)-one having a melting point of 95°–96° C.

The starting material can be manufactured as follows:

Solutions of 12 g (0.3 mole) of sodium hydroxide in 90 ml of water and 32.7 g (0.39 mole) of freshly distilled 3-penten-2-one in 210 ml of methanol are added in direct succession to a mixture of 51.2 g (0.3 mole) of the hydrochloride of imidazo[1,2-a]pyridin-2(3H)-one in 120 ml of water. After stirring at room temperature for 30 hours, the mixture is concentrated to dryness by evaporation in vacuo at approximately 45° C., the residue is taken up in 360 ml of glacial acetic acid and, after the addition of 32.4 g (0.33 mole) of maleic acid anhydride and 12 g of sodium acetate, the mixture is boiled under reflux until $CO_2$ evolution is complete. The solvent is removed in vacuo, and the crude product is taken up in a mixture of 180 ml of 6 M sulphuric acid and 180 ml of tetrahydrofuran and maintained at 60° C. for 8 hours. After removing tetrahydrofuran in vacuo, the mixture is diluted with water and extracted with methylene chloride. The organic phase is dried and concentrated by evaporation and the residue is chromatographed over silica gel with petroleum ether/methylene chloride. The subsequent distillation (100° C./6.10$^{-2}$ torr) yields 4-methyl-3-(1-methyl-3-oxobutyl)-maleic acid anhydride in the form of a pale-yellow oil.

EXAMPLE 8

A cold solution of chlorine in chloroform is added dropwise at from 0° to 5° C., while stirring, to a mixture of 14.7 g (0.063 mole) of 3-methyl-6-morpholinobenzofuran-2(3H)-one in 100 ml of chloroform until no more educt is visible in the thin layer chromatograph. The reaction mixture is diluted with methylene chloride and washed in succession with 10% strength sodium thiosulphate solution, dilute sodium bicarbonate solution and water. The crude product remaining after drying and concentrating by evaporation the organic phase is chromatographed over silica gel with petroleum ether/ether. Recrystallisation of the pure fractions from ether/petroleum ether yields 5-chloro-3-methyl-6-morpholinobenzofuran-2(3H)-one having a melting point of 103°–105° C.

EXAMPLE 9

In a manner analogous to that described in Example 8, using as starting materials 3-methyl-6-(piperidin-1-yl)-benzofuran-2(3H)-one and chlorine, 5-chloro-3-methyl-6-(piperidin-1-yl)-benzofuran-2(3H)-one having a melting point of 112°–113° C. is obtained.

EXAMPLE 10

In a manner analogous to that described in Example 8, using as starting materials 3-methyl-6-(pyrrolidin-1-yl)-benzofuran-2(3H)-one and chlorine, 5-chloro-3-methyl-6-(pyrrolidin-1-yl)-benzofuran-2(3H)-one having a melting point of 60°–62° C. is obtained.

EXAMPLE 11

A solution of 11 g (0.069 mole) of bromine in 50 ml of chloroform is added dropwise in the course of one hour, at from 0° to 5° C. while stirring, to a mixture of 15 g (0.064 mole) of 3-methyl-6-morpholinobenzofuran-2(3H)-one in 120 ml of chloroform. Subsequently the mixture is stirred at room temperature for 30 minutes. Methylene chloride is added to the reaction mixture, which is washed in succession with 10% strength sodium thiosulphate solution, dilute sodium bicarbonate solution and water. The crude product remaining after drying and concentrating by evaporation the organic phase is chromatographed over silica gel with petroleum ether/ether. Recrystallisation of the pure fractions from ether/petroleum ether yields 5-bromo-3-methyl-6-morpholinobenzofuran-2(3H)-one having a melting point of 99°–100° C.

EXAMPLE 12

In a manner analogous to that described in Example 11, using as starting materials 3-methyl-6-(pyrrolidin-1-yl)-benzofuran-2(3H)-one and bromine, 5-bromo-3-methyl-6-(pyrrolidin-1-yl)-benzofuran-2(3H)-one having a melting point of 73°–75° C. is obtained.

EXAMPLE 13

In a manner analogous to that described in Example 11, using as starting materials 3,4-dimethyl-6-morpholino-benzofuran-2(3H)-one and bromine, 5-bromo-3,4-dimethyl-6-morpholinobenzofuran-2(3H)-one having a melting point of 146°–149° C. (decomposition) is obtained.

EXAMPLE 14

A solution of 6.5 g (31.5 mmoles) of dicyclohexylcarbodiimide in 40 ml of absolute methylene chloride is added at room temperature in the course of approximately 3 minutes to a solution of 8.1 g (30 mmoles) of crude 5-chloro-2-hydroxy-4-(piperidin-1-yl)-phenylacetic acid in 50 ml of absolute methylene chloride. The reaction mixture is stirred at room temperature for 30 minutes. The precipitated dicyclohexylurea is filtered off with suction and washed with methylene chloride. The filtrate is concentrated by evaporation in a vacuum rotary evaporator and the residue is chromatographed over silica gel with the eluant methylene chloride/hexane (1:1). Recrystallisation from hexane yields 5-chloro-6-(piperidin-1-yl)-benzofuran-2(3H)-one having a melting point of 129°–131° C.

6-(4-morpholino)-benzofuran-2(3H)-one having a melting point of 153°–155° C. is obtained in an analogous manner.

The starting material can be manufactured as follows:

A solution of 96 g (0.72 mole) of aluminium trichloride in 180 ml of absolute nitromethane is added dropwise in the course of approximately 30 minutes, under a nitrogen atmosphere and while cooling with ice/methanol, to a mixture of 106.2 g (0.60 mole) of 3,4-dichloroanisole [H. Jamarlik et al., Comptes Rendus Acad. Sci. Ser. C 273 (25), 1756 (1971)] and 51.1 ml (0.72 mole) of acetyl chloride in such a manner that the internal temperature range is between 0° and 5°. Subsequently the mixture is stirred for a further hour at approximately from 4° to 6°, and is then poured onto ice and extracted with methylene chloride. The organic extracts are washed with water, combined, dried over sodium sulphate and concentrated by evaporation in a vacuum rotary evaporator. Recrystallisation from methanol/water yields 4,5-dichloro-2-methoxyacetophenone having a melting point of 93°–95° C.

A solution of 76.7 g (0.35 mole) of 4,5-dichloro-2-methoxyacetophenone in 750 ml of piperidine is maintained at 170° in the autoclave for 7 hours. The reaction mixture is concentrated by evaporation, taken up in ethyl acetate and wahed with water. The ethyl acetate extracts are combined, dried over sodium sulphate and concentrated by evaporation in a vacuum rotary evaporator. The residue is chromatographed over silica gel with methylene chloride. In this manner 5-chloro-2-hydroxy-4-(piperidin-1-yl)-acetophenone having a melting point of 68°–70° C. is obtained.

5-chloro-2-hydroxy-4-(4-morpholino)-acetophenone having a melting point of 102°–103° C. is obtained in an analogous manner.

A solution of 32.5 g (128 mmoles) of 5-chloro-2-hydroxy-4-(N-piperidino)-acetophenone with 75 ml (166 mmoles) of an approximately 40% methanolic solution of benzyltriethylammonium hydroxide (Triton B) in 65 ml of tetrahydrofuran is cooled to 0°. In the course of approximately 6 minutes, 14.6 ml (154 mmoles) of dimethyl sulphate are added dropwise in such a manner that the internal temperature does not exceed 5°. The reaction mixture is stirred for a further hour at 0°, then is boiled under reflux for approximately 30 minutes. The reaction mixture is then poured into 400 ml of water and extracted with ethyl acetate. The combined ethyl acetate phases are washed with water, dried over sodium sulphate and concentrated by evaporation in a vacuum rotary evaporator. The residue is recrystallised from methylene chloride/hexane, yielding 5-chloro-2-methoxy-4-(piperidin-1-yl)-acetophenone having a melting point of 119°–120°.

5-chloro-2-methoxy-4-(4-morpholino)-acetophenone having a melting point of 143°–145° is obtained in an analogous manner.

A solution of 18.2 g (68 mmoles) of 5-chloro-2-methoxy-4-(piperidin-1-yl)-acetophenone and 4.36 g (136 mmoles) of sulphur in 68 ml of morpholine is maintained at 90° for 5 hours. The reaction mixture is cooled, diluted with ethyl acetate and washed with water. The combined ethyl acetate extracts are dried over sodium sulphate and concentrated by evaporation in a vacuum rotary evaporator. Recrystallisation from methylene chloride/methanol yields 5-chloro-2-methoxy-4-(piperidin-1-yl)-phenylthioacetic acid morpholinamide having a melting point of 137°–139°.

5-chloro-2-methoxy-4-(4-morpholino)-phenylthioacetic acid morpholinamide having a melting point of 160°–162.5° is obtained in an analogous manner.

A solution of 11.07 g (30 mmoles) of 5-chloro-2-methoxy-4-(piperidin-1-yl)-phenylthioacetic acid morpholinamide in 120 ml of glacial acetic acid and 30 ml of concentrated hydrochloric acid is boiled under reflux for 22 hours. The reaction mixture is cooled, diluted with water and extracted with methylene chloride. The combined methylene chloride phases are washed with water, dried over sodium sulphate and concentrated by evaporation in a high vacuum rotary evaporator. Chromatography over silica gel with chloroform/methanol (19:1) yields 5-chloro-2-methoxy-4-(piperidin-1-yl)-phenylacetic acid which, after recrystallisation with methylene chloride/hexane, melts at 120°–122°.

5-chloro-2-methoxy-4-(4-morpholino)-phenylacetic acid having a melting point of 141°–143° is obtained in an analogous manner.

A solution of 8.5 g (30 mmoles) of 5-chloro-2-methoxy-4-(piperidin-1-yl)-phenylacetic acid in 150 ml of 48% strength hydrobromic acid is boiled under reflux for 15 hours. The reaction mixture is cooled, diluted with water and adjusted to a pH of 3–4 with saturated sodium bicarbonate solution. The mixture is then extracted with ethyl acetate, and the combined organic phases are washed with water, dried over sodium sulphate and concentrated by evaporation in a high vacuum rotary evaporator. There is obtained a dark-grey foam comprising 5-chloro-2-hydroxy-4-(piperidin-1-yl)-phenylacetic acid, which is reacted, without being purified, to form 5-chloro-6-(piperidin-1-yl)-benzofuran-2(3H)-one.

2-hydroxy-4-(4-morpholino)-phenylacetic acid is obtained in an analogous manner.

EXAMPLE 15

7 ml (0.045 mole) of 2,5-dimethoxytetrahydrofuran and 5 ml of 5 N HCl are added to a solution of 6.7 g (0.035 mole) of 6-amino-5-chloro-3-methylbenzofuran-2(3H)-one in 100 ml of dioxane. After 1 hour, the aqueous phase that has formed is removed and the upper dioxane-containing phase is concentrated to dryness by evaporation in vacuo. The dark-brown residue is filtered with methylene chloride through silica gel. After evaporating the methylene chloride, 5-chloro-3-methyl-6-(pyrrol-1-yl)-benzofuran-2(3H)-one is obtained in the form of colourless prisms having a melting point of 100°–101°.

The starting material can be manufactured as follows:

In a manner analogous to that described in Example 1, using as starting materials 4-methyl-3-(3-oxobutyl)-maleic acid anhydride and dibenzylammonium benzoate, 6-dibenzylamino-3-methylbenzofuran-2(3H)-one is obtained in the form of a colourless oil.

In a manner analogous to that described in Example 8, using as starting materials 6-dibenzylamino-3-methyl-benzofuran-2(3H)-one and chlorine, 5-chloro-6-dibenzylamino-3-methylbenzofuran-2(3H)-one having a melting point of 111°–112° is obtained.

A solution of 21.8 g (0.058 mole) of 5-chloro-6-dibenzylamino-3-methylbenzofuran-2(3H)-one in 220 ml of dioxane is reduced with 2.0 g of palladium-on-carbon (5% strength) at room temperature with hydrogen without superatmospheric pressure. After absorption of the theoretical amount of hydrogen the catalyst is removed by filtration and the dioxane is evaporated off in vacuo. 20 ml of cold methanol are added to the residue and the precipitate is filtered off. 6-amino-5-chloro-3-methylbenzofuran-2(3H)-one is obtained in the form of colourless crystals having a melting point of 139°–140°.

EXAMPLE 16

A mixture of 15.7 g (0.08 mole) of 4-methyl-3-(2-methyl-3-oxobutyl)-maleic acid anhydride and 20.3 g (0.092 mole) of hexahydroazepinium benzoate in 400 ml of benzene is heated under reflux for 48 hours using a water separator. After the addition of a further 3.3 g (15 mmoles) of hexahydroazepinium benzoate, the reaction mixture is left to reflux for a further 24 hours using the water separator. Subsequently, the benzene is removed in vacuo and the residue is partitioned between methylene chloride and saturated sodium bicarbonate solution. The crude product remaining after drying and after removal of the methylene chloride is chromatographed over silica gel with petroleum ether/ether. Subsequent distillation in a bulb tube (150° C./6.10$^{-2}$ torr) yields a pale-yellow oil, which crystallises on standing. Recrystallisation from petroleum ether yields 3,5-dimethyl-6-(hexahydroazepin-1-yl)-benzofuran-2(3H)-one having a melting point of 58°–60° C.

EXAMPLE 17

A mixture of 19.6 g (0.1 mole) of 4-methyl-3-(2-methyl-3-oxobutyl)-maleic acid anhydride and 21.7 g (0.105 mole) of piperidinium benzoate in 400 ml of benzene is heated under reflux for 48 hours using a water separator. The benzene is removed in vacuo and the residue is partitioned between methylene chloride and saturated sodium bicarbonate solution. The crude product remaining after drying and after removal of the methylene chloride is chromatographed over silica gel with petroleum ether/ether. Subsequent recrystallisation from petroleum ether yields 3,5-dimethyl-6-(piperidin-1-yl)-benzofuran-2(3H)-one having a melting point of 61°–63° C.

EXAMPLE 18

A mixture of 12.6 g (0.06 mole) of 3-(2-ethyl-3-oxobutyl)-4-methylmaleic acid anhydride and 12.2 g (0.063 mole) of pyrrolidinium benzoate in 200 ml of benzene is heated under reflux for 24 hours using a water separator. The benzene is then removed in vacuo and the residue that remains is partitioned between methylene chloride and saturated sodium bicarbonate solution. The crude product remaining after drying and after removal of the methylene chloride is chromatographed over silica gel with petroleum ether/ether. Subsequent distillation in a bulb tube (140° C./6.10$^{-2}$ torr) yields 5-ethyl-3-methyl-6-(pyrrolidin-1-yl)-benzofuran-2(3H)-one in the form of a pale-yellow oil.

The starting material can be manufactured as follows:

A mixture of 86 g (0.3 mole) of the hydrochloride of 3-(1,2-dicarboxyethyl)-imidazo[1,2-a]pyridin-2(3H)-one, 41.2 g (0.42 mole) of 3-ethyl-3-buten-2-one, 110 ml of methanol and 110 ml of water is stirred at room temperature for 36 hours, and is then concentrated to dryness by evaporation in vacuo at approximately 45° C. The resulting crude product is taken up in 225 ml of glacial acetic acid, 11 g of sodium acetate are added and the whole is boiled under reflux until $CO_2$ evolution is complete. Then, the solvent is removed in vacuo, a mixture of 110 ml of 6 M sulphuric acid and 110 ml of tetrahydrofuran is added to the residue and the whole is heated under reflux for 8 hours. After removing tetrahydrofuran in vacuo, the reaction mixture is diluted with water and extracted with methylene chloride. The crude product remaining after drying and concentrating by evaporation the organic phase is chromatographed over silica gel with methylene chloride. Subsequent distillation (110°–120° C./10$^{-1}$ torr) yields 3-(2-ethyl-3-oxobutyl)-4-methylmaleic acid anhydride in the form of a pale-yellow oil.

EXAMPLE 19

A mixture of 15.3 g (0.065 mole) of 4-methyl-3-(1,2-tetramethylene-3-oxobutyl)-maleic acid anhydride and 13.5 g (0.07 mole) of pyrrolidinium benzoate in 400 ml of benzene is heated under reflux for 60 hours using a water separator. The benzene is removed in vacuo and the residue is partitioned between methylene chloride and saturated sodium bicarbonate solution. The crude product remaining after drying and after removal of the methylene chloride is chromatographed over silica gel with petroleum ether/ether. Subsequent recrystallisation from ether/petroleum ether yields 3-methyl-6-(pyrrolidin-1-yl)-4,5-tetramethylenebenzofuran-2(3H)-one having a melting point of 99°–101° C.

The starting material can be manufactured as follows:

Solutions of 13.2 g (0.33 mole) of sodium hydroxide in 90 ml of water and 48.4 g (0.39 mole) of 1-acetylcyclohexene in 210 ml of methanol are added in direct succession to a mixture of 51.2 g (0.3 mole) of the hydrochloride of imidazo[1,2-a]pyridin-2(3H)-one in 120 ml of water. After stirring at room temperature for 24 hours, the mixture is concentrated to dryness by evaporation in vacuo at approximately 45° C., the residue is taken up in 240 ml of glacial acetic acid and, after the addition of 29.4 g (0.3 mole) of maleic acid anhydride and 7.5 g of sodium acetate, the mixture is boiled under reflux until $CO_2$ evolution is complete. The solvent is distilled off in vacuo, and the crude product is taken up in a mixture of 180 ml of 6 M sulphuric acid and 180 ml of tetrahydrofuran and heated under reflux for 8 hours. After removing tetrahydrofuran in vacuo, the mixture is diluted with water and extracted with methylene chloride. The organic phase is dried and concentrated by evaporation and the residue is chromatographed over silica gel with petroleum ether/methylene chloride. Subsequent distillation (110°–115° C./10$^{-1}$ torr) yields 4-methyl-3-(1,2-tetramethylene-3-oxobutyl)-maleic acid anhydride in the form of a pale-yellow oil.

EXAMPLE 20

In the course of 5 minutes, 18 g (0.13 mole) of 2,5-dimethoxytetrahydrofuran are added dropwise at from 104°–106°, while stirring, to a solution of 18 g (0.1 mole) of 6-amino-3,5-dimethylbenzofuran-2(3H)-one in 200 ml of acetic acid (96% strength) and the mixture is then stirred for 5 minutes at that temperature. Subsequently, the mixture is rapidly cooled and the solvent is removed in vacuo. The residue is partitioned between ether and water, and the ethereal phase is washed with saturated sodium bicarbonate solution, dried and concentrated by evaporation in vacuo. The crude residue is chromatographed over silica gel with methylene chloride. The pure eluates, comprising 3,5-dimethyl-6-(pyrrol-1-yl)-benzofuran-2(3H)-one, are distilled in a high vacuum, b.p. (0.01 torr) 190°. The distillate melts at 61°–63°.

EXAMPLE 21

A mixture of 19.6 g (0.1 mole) of 4-methyl-3-(2-methyl-3-oxobutyl)-maleic acid anhydride and 20 g (0.105 mole) of 3-pyrrolinium benzoate in 250 ml of benzene is heated under reflux for 5 hours using a water separator. Then, the benzene is evaporated off in vacuo and the residue is partitioned between ether and 1 N hydrochloric acid. The organic phase is washed with water and saturated sodium bicarbonate solution, dried and concentrated. The crude product so-obtained is chromatographed over silica gel with diisopropyl ether. The resulting pure eluates are recrystallised from diisopropyl ether. In this manner 3,5-dimethyl-6-(3-pyrrolin-1-yl)-benzofuran-2(3H)-one having a melting point of 81°–82° is obtained.

EXAMPLE 22

4 g (0.01 mole) of 2-[5-methyl-2-hydroxy-4-(indolin-1-yl)-phenyl]-propionic acid indolinamide are distilled under a high vacuum at 0.001 torr and 200° to 220°. The distillate is partitioned between ether and 1 N hydrochloric acid. After drying and after evaporating off the ether, a yellow oil is obtained which is chromatographed over silica gel with methylene chloride. The 3,5-dimethyl-6-(indolin-1-yl)-benzofuran-2(3H)-one so obtained is distilled in a high vacuum, b.p. (0.001 torr) 220°.

The starting material can be obtained as follows:

A mixture of 19.6 g (0.1 mole) of 4-methyl-3-(2-methyl-3-oxobutyl)-maleic acid anhydride and 48.2 g of indolinium benzoate in 52 ml of benzene is heated under reflux for 6 hours using a water separator. Subsequently, the benzene is evaporated off in vacuo and the residue is partitioned between ether and 1 N hydrochloric acid. The organic phase is washed with saturated sodium bicarbonate solution and, after drying, is concentrated. The crude 2-[5-methyl-2-hydroxy-4-(indolin-1-yl)-phenyl]-propionic acid indolinamide so obtained melts at 176°-178° and is further processed directly.

EXAMPLE 23

5.9 g (0.026 mole) of 2,3-dicyano-5,6-dichloro-benzoquinone, dissolved in 100 ml of dioxane, are added dropwise in the course of 45 minutes at from 20° to 25°, while stirring and under a nitrogen atmosphere, to a solution of 6 g (0.024 mole) of 3,5-dimethyl-6-(indolin-1-yl)-benzofuran-2(3H)-one in 50 ml of dioxane, and the mixture is then stirred at room temperature for 16 hours. Subsequently, the precipitate is filtered off and the solvent is evaporated off in vacuo. The crude product so obtained is chromatographed over silica gel with methylene chloride and the pure eluates are distilled together in a high vacuum. In this manner 3,5-dimethyl-6-(indol-1-yl)-benzofuran-2(3H)-one, b.p. (0.001 torr) 220° C., is obtained.

A mixture of 2.3 g (0.01 mole) of 3,5-dimethyl-6-(pyrrol-1-yl)-3a,6-dihydrobenzofuran-2(3H)-one and 13.6 g (0.06 mole) of 2,3-dicyano-5,6-dichlorobenzoquinone in 50 ml of dioxane is heated under reflux for 5 hours while stirring. After cooling, the mixture is filtered and the dioxane is evaporated off in vacuo.

The resulting crude product is chromatographed over silica gel with methylene chloride and crystallised from butanol. The 3,5-dimethyl-6-(pyrrol-1-yl)-benzofuran-2(3H)-one so obtained melts at 61°-63°. The starting material can be obtained, for example, as follows:

A mixture of 19.6 g (0.1 mole) of 4-methyl-3-(2-methyl-3-oxobutyl)-maleic acid anhydride and 20 g (0.105 mole) of 3-pyrrolinium benzoate in 250 ml of benzene is heated under reflux for 5 minutes using a water separator. The benzene is evaporated off in vacuo and the residue is partitioned between ether and saturated sodium bicarbonate solution. The crude product remaining after drying and concentrating by evaporation the organic phase is chromatographed over silica gel. Elution with diisopropyl ether and subsequent recrystallisation of the pure fractions from isopropyl ether yields 3,5-dimethyl-6-(pyrrol-1-yl)-3a,6-dihydrobenzofuran-2(3H)-one having a melting point of 116°-117°.

EXAMPLE 25

A mixture of 9.5 g (0.05 mole) of 4-methyl-3-(2-methyl-3-oxobutyl)-maleic acid anhydride and 17.9 g (0.08 mole) of cis-3,4-dimethylpyrrolidinium benzoate in 250 ml of benzene is heated under reflux for 24 hours using a water separator. Subsequently, the benzene is evaporated off in vacuo and the residue is partitioned between ether and 1 N hydrochloric acid. The organic phase is washed with water and saturated sodium bicarbonate solution, dried and concentrated. The crude product so obtained is chromatographed over silica gel with methylene chloride, and the pure eluates are distilled in a high vacuum. In this manner, 3,5-dimethyl-6-(cis-3,4-dimethylpyrrolidin-1-yl)-benzofuran-2(3H)-one having a b.p. (0.001 torr) of 210° is obtained.

In an analogous manner, using as starting materials 4-methyl-3-(2-methyl-3-oxobutyl)-maleic acid anhydride and trans-3,4-dimethylpyrrolidinium benzoate, there are obtained a pure stereoisomer of 3,5-dimethyl-6-(trans-3,4-dimethylpyrrolidin-1-yl)-benzofuran-2(3H)-one having a melting point of 104°-105° and a stereoisomeric mixture having a melting point of 62°-77°.

EXAMPLE 26

A mixture of 1.8 g (6 mmoles) of 2-[2-hydroxy-5-methyl-4-(pyrrolidin-1-yl)-phenyl]-propionic acid pyrrolidide, 2 ml of glacial acetic acid and 2 ml of concentrated hydrochloric acid is boiled under reflux for 40 minutes. The reaction mixture is concentrated by evaporation in vacuo, water is added to the residue, the pH is adjusted to 5 with dilute sodium hydroxide solution and extraction with ether is carried out 3 times. The combined ethereal extracts are dried over sodium sulphate and concentrated in vacuo to 10 ml. 1.2 g (6 mmoles) of N,N'-dicyclohexylcarbodiimide are added thereto and the mixture is left at room temperature for one hour; the residue is filtered off, subsequently washed with ether, and the filtrate is concentrated by evaporation in vacuo. The residue is chromatographed over silica gel with petroleum ether/ether. Subsequent recrystallisation of the pure fractions from ether/petroleum ether yields 3,5-dimethyl-6-(pyrrolidin-1-yl)-benzofuran-2(3H)-one having a melting point of 68°-69°. The starting material can be obtained, for example, as follows:

42.6 ml (0.6 mole) of acetyl chloride are added dropwise in the course of 1 hour at room temperature, while stirring, to 81.1 g (0.5 mole) of 4-methyl-2-(1-methyl-2-propenyl)-phenol. The reaction mixture is then heated to 100° and left at this temperature for 2 hours. After cooling, water is cautiously added and extraction is carried out with methylene chloride. The organic phase is dried over sodium sulphate and concentrated by evaporation. Subsequent distillation of the remaining residue (64°-70°/$4.10^{-2}$ torr) yields 4-methyl-2-(1-methyl-2-propenyl)-phenyl acetate in the form of a pale-yellow oil.

A mixture of 20.4 g (0.1 mole) of 4-methyl-2-(1-methyl-2-propenyl)-phenyl acetate and 100 mg (0.4 mmole) of osmium tetroxide in 300 ml of dioxane and 100 ml of water is stirred at room temperature for 30 minutes, then, in the course of 30 minutes, 42.8 g (0.2 mole) of sodium periodate are added in portions and the mixture is subsequently stirred for one hour. The resulting precipitate is filtered off and then washed with dioxane/water (1:1). The aqueous-organic phase is concentrated in vacuo to approximately one third and extracted with methylene chloride. The oily crude product obtained after drying and after removal of the methylene chloride is taken up in 100 ml of acetone and oxidised by adding dropwise in the course of half an hour a solution of 7.2 g (72 mmoles) of chromium trioxide and 6.2 ml of concentrated sulphuric acid in 40 ml of water. Subsequently, 3 ml of methanol and 200 ml of water are added, the acetone is removed in vacuo, the aqueous phase is extracted with ether and the ther solution is extracted three times with 10% sodium hydroxide solution. The aqueous alkaline solution is left to stand at room temperature for 3 hours, then adjusted to pH 3 with concentrated hydrochloric acid and extracted with ether. The oil obtained after drying and after removal of the ether is stirred for 2 hours with 300 ml of saturated methanolic hydrochloric acid. Subsequently, the methanol is removed in vacuo and the residue is partitioned between ether and dilute sodium bicarbonate solution. The crude product obtained after drying and concentrating by evaporation the organic phase is chromatographed over silica gel with methylene chloride. Subsequent recrystallisation of the pure fractions from methylene chloride/petroleum ether yields 2-(2-hydroxy-5-methylphenyl)-propionic acid methyl ester having a melting point of 104°–106°.

A mixture of 5.8 g (30 mmoles) of 2-(2-hydroxy-5-methylphenyl)-propionic acid methyl ester, 36.5 g (82 mmoles) of lead tetraacetate and 150 ml of glacial acetic acid is stirred at room temperature for 36 hours. The glacial acetic acid is removed in vacuo and 300 ml of water are added to the residue. The resulting precipitate is filtered off and washed thoroughly with ether. The filtrate is extracted with ether. The combined ethereal phases are dried over sodium sulphate and concentrated by evaporation in vacuo. The reddish oil which remains is taken up in 80 ml of dioxane, 8.7 ml (106 mmoles) of pyrrolidine are added thereto and the mixture is boiled under reflux for 5 hours. The dioxane is removed in vacuo and the residue is chromatographed over silica gel with methylene chloride/acetone. Recrystallisation of the pure fractions from acetone yields 2-[2-hydroxy-5-methyl-2-(pyrrolidin-1-yl)-phenyl]-propionic acid pyrrolidide having a melting point of 178°–180°.

EXAMPLE 27

3.8 g (0.1 mole) of sodium borohydride are added in portions, while stirring, to a methanolic solution of 26.9 g (0.1 mole) of 5-chloro-2-methoxy-4-morpholino-acetophenone and the mixture is stirred for 1 hour at room temperature. The methanolic solution is concentrated in a vacuum rotary evaporator and the residue is partitioned between dilute dydrochloric acid and methylene chloride. The organic phases are combined, dried over sodium sulphate and concentrated by evaporation. The residue is taken up in 60 ml of absolute methylene chloride and added dropwise in the course of 2 hours under a nitrogen atmosphere to a mixture of 17.8 g (0.15 mole) of thionyl chloride and 120 ml of absolute methylene chloride. The mixture is then stirred for a further hour, the solvent is concentrated in a vacuum rotary evaporator and the residue is partitioned between sodium bicarbonate solution and methylene chloride. The organic phases are washed neutral, combined, dried over sodium sulphate and concentrated. The residue is taken up in 100 ml of absolute tetrahydrofuran and added dropwise to a suspension of 2.4 g (0.1 g/atom) of magnesium turnings in 20 ml of absolute tetrahydrofuran in such a manner that the reaction mixture boils gently under reflux. The mixture is then further boiled under reflux for another 2 hours. The solution, cooled to room temperature, is cautiously added dropwise to approximately 50 g of dry ice covered with a layer of absolute tetrahydrofuran. The reaction mixture is heated to room temperature, acidified with dilute hydrochloric acid and extracted 3 times with methylene chloride. The organic phases are washed neutral, combined, dried over sodium sulphate and concentrated in a vacuum rotary evaporator. Recrystallisation of the crude product from ethyl acetate/petroleum ether yields 2-(5-chloro-2-methoxy-4-morpholinophenyl)-propionic acid having a melting point of 164°–165°.

8.99 g of 2-(5-chloro-2-methoxy-4-morpholinophenyl)-propionic acid (0.03 mole) are boiled in 48% hydrogen bromide solution for 2 hours. The reaction mixture is cooled and concentrated and extracted 3 times with methylene chloride. The organic phases are washed neutral, combined, dried over sodium sulphate and concentrated in a vacuum rotary evaporator. In this manner 5-chloro-3-methyl-6-(morpholin-4-yl)-benzofuran-2(3H)-one having a melting point of 103°–105° is obtained.

EXAMPLE 28

A solution of 2.5 g (10 mmoles) of 5-chloro-6-(piperidin-1-yl)-benzofuran-2(3H)-one and 2.1 g (15 mmoles) of methyl iodide in 15 ml of absolute 1,2-dimethoxyethane is added dropwise in the course of 20 minutes to a suspension, boiling under nitrogen, of 530 mg (11 mmoles) of 50% strength sodium hydride-oil dispersion in 15 ml of absolute 1,2-dimethoxyethane. The mixture is then boiled under reflux for a further 3 hours, the solvent is removed in vacuo and the residue is cautiously acidified with dilute hydrochloric acid and extracted three times with methylene chloride. The organic phases are washed with water, combined, dried over sodium sulphate and concentrated in a vacuum rotary evaporator. Recrystallisation from ether/petroleum ether yields 5-chloro-3-methyl-6-(piperidin-1-yl)-benzofuran-2(3H)-one having a melting point of 112°–113°.

EXAMPLE 29

A solution of 2.5 g (10 mmoles) of 5-chloro-6-(piperidin-1-yl)-benzofuran-2(3H)-one in 15 ml of absolute 1,2-dimethoxyethane is added dropwise in the course of 20 minutes to a suspension, boiling under nitrogen, of 530 mg (11 mmoles) of 50% strength sodium hydride-oil dispersion in 15 ml of absolute 1,2-dimethoxyethane. The mixture is then boiled under reflux for a further 3 hours. It is then cooled to −20° and anhydrous formaldehyde gas is introduced by means of nitrogen.

After stirring for a further 30 minutes, the mixture is hydrolysed with dilute hydrochloric acid and the product is extracted with ether. The ether extracts are washed with water, combined, dried over sodium sulphate and concentrated. The residue, 5-chloro-3-hydroxymethyl-6-(piperidin-1-yl)-benzofuran-2(3H)-one, is taken up in 30 ml of absolute pyridine and 2.1 g (11 mmoles) of tosyl chloride are added. After stirring for 24 hours at room temperature, the reaction mixture is heated under reflux for 6 hours. The reaction mixture is cooled, the pyridine is concentrated in a vacuum rotary evaporator and the residue is partitioned between dilute hydrochloric acid and methylene chloride. The organic phases are washed neutral with bicarbonate solution and with water, combined, dried over sodium sulphate and concentrated. The residue is dissolved in 20 ml of dioxane, 200 ml of palladium-on-carbon (10% strength) are added and hydrogenation is carried out at room temperature. The catalyst is filtered off, the filtrate is concentrated and the residue is recrystallised from ether/petroleum ether. 5-chloro-3-methyl-6-(piperidin-1-yl)-benzofuran-2(3H)-one having a melting point of 108°–111° is obtained.

EXAMPLE 30

2.27 g (11 mmoles) of dicyclohexylcarbodiimide in 20 ml of absolute methylene chloride are added at room temperature to a solution of 2.5 g (10 mmoles) of 2-[2- hydroxy-5-methyl-4-(pyrrol-1-yl)-phenyl]-propionic acid in 30 ml of absolute methylene chloride. The reaction mixture is stirred for approximately 30 minutes at room temperature, the precipitate is filtered off and the filtrate is concentrated in a vacuum rotary evaporator. Distillation yields 3,5-dimethyl-6-(pyrrol-1-yl)-benzofuran-2(3H)-one, b.p. 180°/0.005 torr, m.p. 61°–63°.

The starting material can be manufactured, for example, as follows:

12.4 g of palladium-on-carbon are added to a solution of 132.9 g (0.759 mole) of 4-methyl-3-nitro-anisole in 1.1 liters of methanol and hydrogenation is carried out at room temperature. The catalyst is filtered off and the filtrate is concentrated in a vacuum rotary evaporator. Recrystallisation from isopropanol/water yields 3-amino-4-methylanisole having a melting point of 43°–44°.

A solution of 88.4 g (0.64 mole) of 3-amino-4-methylanisole in 1.4 liters of glacial acetic acid is heated to 106° and, at this temperature, 114 g (0.86 mole) of 2,5-dimethoxytetrahydrofuran are added in the course of 30 minutes. The mixture is then immediately cooled to room temperature and concentrated in a vacuum rotary evaporator. Distillation of the residue in a high vacuum yields 4-methyl-3-(pyrrol-1-yl)-anisole, b.p. 93°–95°/0.04 torr. $R_f$ (toluene/ethyl acetate=10:1): 0.57.

A solution of 86.6 g (0.46 mole) of 4-methyl-3-(pyrrol-1-yl)-anisole in 1.5 liters of absolute methylene chloride is cooled to −78° with acetone/dry ice. At this temperature, 231.7 g (0.92 mole) of boron tribromide are added dropwise. Subsequently, the cooling bath is removed and the reaction mixture is heated to from 0° to 5°, then poured into 2 liters of ice/water, and the methylene chloride phase is removed and washed with saturated sodium chloride solution. The aqueous phases are then extracted a further twice with methylene chloride. The organic phases are combined, dried over sodium sulphate and concentrated in a vacuum rotary evaporator. Distillation of the residue in a high vacuum yields 4-methyl-3-(pyrrol-1-yl)-phenol, b.p. 105°–107°/0.03 torr, $R_f$ (toluene/ethyl acetate=10:1): 0.38.

45.7 g (0.39 mole) of crotyl bromide are added in the course of one hour to a suspension of 53.4 g (0.31 mole) of 4-methyl-3-(pyrrol-1-yl)-phenol and 53.7 g (0.39 mole) of potassium carbonate in 60 ml of absolute acetone under reflux and the mixture is then boiled for a further 4½ hours. The reaction mixture is cooled and diluted with 800 ml of water. The acetone is evaporated off in a vacuum rotary evaporator and the residue is repeatedly extracted with methylene chloride. The organic phases are washed with water, combined and dried over sodium sulphate and concentrated in a vacuum rotary evaporator. Brief filtration over approximately 800 g of silica gel with methylene chloride yields 1-[4-methyl-3-(pyrrol-1-yl)]-phenoxy-2-butene in the form of a pale-yellow oil, $R_f$(hexane/ether=9:1): 0.45, $R_f$(toluene/ethyl acetate=10:1): 0.68.

A solution of 60 g (0.26 mole) of 1-[4-methyl-3-(pyrrol-1-yl)]-phenoxy-2-butene in 170 ml of absolute N,N-diethylaniline is boiled under reflux for 5 hours. The reaction mixture is cooled, diluted with methylene chloride and acidified with 6 N hydrochloric acid. The aqueous phase is removed and extracted again with methylene chloride. The organic phases are washed neutral, combined, dried over sodium sulphate and concentrated in a vacuum rotary evaporator. Chromatography over silica gel with hexane/ether (9:1) yields 3-[2-hydroxy-5-methyl-4-(pyrrol-1-yl)-phenyl]-1-butene. $R_f$ (hexane/ether=9:1): 0.17, $R_f$ (toluene/ethyl acetate=10:1): 0.45.

A few drops of pyridine are added to a solution of 26.7 g (0.12 mole) of 3-[2-hydroxy-5-methyl-4-(pyrrol-1-yl)-phenyl]-1-butene in 370 ml of acetic anhydride and the mixture is stirred at room temperature for 2 hours. The reaction mixture is poured onto ice and extracted three times with methylene chloride. The methylene chloride phases are washed with dilute sodium bicarbonate solution, then with water, until neutral, are combined, dried over sodium sulphate and concentrated in a vacuum rotary evaporator. Filtration over a little silica gel with methylene chloride yields 3-[2-acetoxy-5-methyl-4-(pyrrol-1-yl)-phenyl]-1-butene, $R_f$ (toluene/ethyl acetate=10:1): 0.55.

A solution of 2.7 g (10 mmoles) of 3-[2-acetoxy-5-methyl-4-(pyrrol-1-yl)-phenyl]-1-butene in 40 ml of absolute methylene chloride is cooled to −78° with acetone/dry ice and ozone is blown through until the blue colour no longer disappears. Then, 2 ml of dimethyl sulphide are added and the cooling bath is removed. The reaction mixture is carefully concentrated in a vacuum rotary evaporator, the residue is dissolved in 50 ml of ethanol, and a solution of 3.7 g (23 mmoles) of silver nitrate in 5 ml of water is added. A solution of 75 ml of a 1 N potassium hydroxide solution is added dropwise to this mixture in the course of approximately 15 minutes. The heterogeneous mixture is further stirred for another 2 hours. The reaction mixture is filtered and the residue is washed with ethanol. The alkaline filtrate is left to stand overnight at room temperature and extracted with methylene chloride. The alkaline solution is cautiously acidified with 6 N hydrochloric acid while cooling and repeatedly extracted with methylene chloride. The organic phases are again washed twice with water, combined, dried over sodium sulphate and concentrated in a vacuum rotary evaporator. Recrystallisation from diisopropyl ether/petroleum ether yields 2-[2-hydroxy-5-methyl-4-(pyrrol-1-yl)phenyl]-propionic acid having a melting point of 73°–74°.

EXAMPLE 31

1.8 g of 6-amino-3,5-dimethylbenzofuran-2-(3H)-one are dissolved in 20 ml of dioxane and, while stirring at room temperature, 2 ml of 2,5-dimethoxy-tetrahydrofuran and 1.4 ml of 37% strength hydrochloric acid are added. After 30 minutes the aqueous phase is removed and the organic phase is concentrated to dryness by evaporation in vacuo. The residue is chromatographed over silica gel with methylene chloride. The resulting pale-yellow oil crystallises from butyl oxide. In this manner 3,5-dimethyl-6-(pyrrol-1-yl)-benzofuran-2(3H)-one having a melting point of 61°–63° C. is obtained.

The starting material can be manufactured as follows:
59 g of 4-methyl-3-(2-methyl-3-oxobutyl)-maleic acid anhydride and 240 g of dibenzylammonium benzoate are boiled under reflux for 48 hours in 1000 ml of benzene using a water separator. Subsequently, the mixture is concentrated to dryness by evaporation in vacuo and the residue is chromatographed over silica gel. The resulting oil crystallised from isopropyl ether. In this manner 2-(4-dibenzylamino-2-hydroxy-5-methylphenyl)-propionic acid dibenzamide having a melting point of 140°–141° C. is obtained.

20 g of 2-(4-dibenzylamino-2-hydroxy-5-methylphenyl)-propionic acid dibenzamide are heated under reflux for 3 hours in 40 ml of 2 N hydrochloric acid and 40 ml of glacial acetic acid. Subsequently, the mixture is concentrated to dryness by evaporation in vacuo and the residue is partitioned between ether and 1 N sodium hydroxide solution. Acidification to a pH of 1 with hydrochloric acid and extraction with ether yields 2-[4-dibenzylamino-2-hydroxy-5-methylphenyl]-propionic acid, which for purification is chromatographed over silica gel with methylene chloride. The colourless crystals melt at 174°–175° C. 5 g of the crystals are dissolved in 50 ml of ether and 6 g of dicyclohexylcarbodiimide are added. After 30 minutes, the urea that has formed is filtered off and the filtrate is concentrated to dryness by evaporation. In this manner 6-dibenzylamino-3,5-dimethyl-benzofuran-2(3H)-one having a melting point of 122°–123° C. is obtained.

4 g of 6-dibenzylamino-3,5-dimethylbenzofuran-2(3H)-one are dissolved in 40 ml of dioxane and reduction is carried out at room temperature, under normal pressure, with hydrogen and with 0.4 g of palladium-on-carbon. The mixture is then filtered, and the filtrate is concentrated to dryness by evaporation and recrystallised from methanol. In this manner 6-amino-3,5-dimethylbenzofuran-2(3H)-one having a melting point of 123°–124° C. is obtained.

EXAMPLE 32

30 g of 2-(4-dibenzylamino-2-hydroxy-5-methylphenyl)-propionic acid benzylamide are distilled in a shortway distiller under high vacuo. The fraction which is distilled at 0.01 torr and 16°–175°, consists of pure 6-dibenzylamino-3,5-dimethyl-benzofuran-2(3H)-one, m.p. 122°–123°.

EXAMPLE 33

A mixture of 5,3 g (0.03 moles) of 6-amino-3,5-dimethyl-benzofuran-2(3H)-one, 4,1 g (0,037 moles) of acetonylacetone, 50 ml of benzene and 0,5 ml of glacial acetic acid is boiled under reflux for 14 hours. After cooling the mixture is washed with water, saturated sodium bicarbonate solution and 1 N hydrochloric acid. Then the benzene is distilled off in vacuo and the residue is chromatographed with methylenechloride over silica gel. After crystallisation of the pure eluate 3,5-Dimethyl-6-(2,5-dimethyl-pyrrol-1-yl)-benzofuran-2(3H)-one is obtained, m.p. 94°–95°.

EXAMPLES 34

Tablets containing 25 mg of active ingredient, for example 3,5-dimethyl-6-(pyrrolidin-1-yl)-benzofuran-2(3H)-one, can be manufactured as follows:

| Constituents (for 1000 tablets) | |
|---|---|
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture

All of the solid ingredients are first of all forced through a sieve having a mesh width of 0.6 mm. Then, the active ingredient, the lactose, the talc, the magnesium stearate and half of the starch are mixed. The other half of the starch is suspended in 40 ml of water, and this suspension is added to a boiling solution of the polyethylene glycol in 100 ml of water. The resulting starch paste is added to the main mixture which is then granulated, if necessary with the addition of water. The granulate is dried overnight at 35°, forced through a sieve having a mesh width of 1.2 mm and compressed into tablets approximately 6 mm in diameter that are concave on both sides.

EXAMPLE 35

Chewing tablets containing 30 mg of active ingredient, for example 5-bromo-3-methyl-6-(pyrrolidin-1-yl)-benzofuran-2(3H)-one, can be manufactured, for example, as follows:

| Composition (for 1000 tablets) | |
|---|---|
| active ingredient | 30.0 g |
| mannitol | 267.0 g |
| lactose | 179.5 g |
| talc | 20.0 g |
| glycine | 12.5 g |
| stearic acid | 10.0 g |
| saccharin | 1.0 g |
| 5% strength gelatine solution | q.s. |

MANUFACTURE

All of the solid ingredients are first of all forced through a sieve having a mesh width of 0.25 mm. The mannitol and the lactose are mixed, granulated with the addition of gelatine solution, forced through a sieve having a mesh width of 2 mm, dried at 50° and forced through another sieve having a mesh width of 1.7 mm. The active ingredient, the glycine and the saccharin are carefully mixed, the mannitol and lactose granulate, the stearic acid and the talc are added, and the whole is thoroughly mixed and compressed into tablets approximately 10 mm in diameter that are concave on both sides and have a break groove on the upper side.

EXAMPLE 36

Tablets containing 100 mg of active ingredient, for example 3,5-dimethyl-6-(pyrrol-1-yl)-benzofuran-2(3H)-one, can be manufactured as follows:

| Composition (for 1000 tablets) | |
|---|---|
| active ingredient | 100.0 g |
| lactose | 248.5 g |
| corn starch | 17.5 g |
| polyethylene glycol 6000 | 5.0 g |
| talc | 15.0 g |
| magnesium stearate | 4.0 g |
| demineralised water | q.s. |

MANUFACTURE

The solid ingredients are first of all forced through a sieve having a mesh width of 0.6 mm. Then, the active ingredient, lactose, talc, magnesium stearate and half the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve having a mesh width of 1.2 mm and compressed into tablets approximately 10 mm in diameter that are concave on both sides and have a break notch on the upper side.

We claim:

1. A method for treating inflammation and pain in warm-blooded animals comprising treating warm-blooded animals in need of such treatment with an effective amount of benzofuranones of the general formula

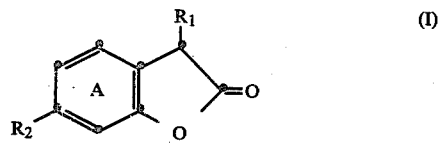

in which $R_1$ represents hydrogen or an aliphatic radical, $R_2$ represents an amino group di-substituted by a divalent hydrocarbon radical, and the aromatic ring A may be additionally substituted, and their salts and/or isomers.

2. The method according to claim 1 wherein $R_1$ represents hydrogen or lower alkyl, $R_2$ represents an amino group di-substituted by lower alkylene, lower alkenylene, aza-lower alkylene, N'-lower alkylaza-lower alkylene, aza-lower alkenylene, N'-lower alkylaza-lower alkenylene, oxa- or thia-lower alkylene or oxa- or thia-lowr alkenylene, wherein lower alkylene and lower alkenylene each have from 4 to 10 carbon atoms and may also be branched and also ortho fused with one or two benzo systems, and the aromatic ring A is additionally mono- or poly-substituted by lower alkyl, hydroxy-lower alkyl, halo-lower alkyl, lower alkenyl, optionally branched 3- or 4-membered alkylene, lower alkoxy, lower alkylthio, lower alkanesulphinyl, lower alkanesulphonyl, hydroxy, halogen, lower alkanoyloxy, lower alkanoyl and/or nitro or, except for $R_2$, is unsubstituted, and their salts, and isomers.

3. The method according to claim 1 wherein the benzofuran has the formula

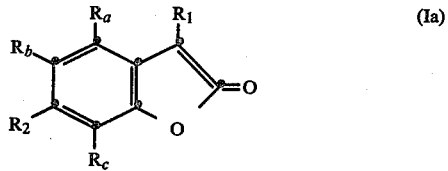

in which $R_1$ represents hydrogen or lower alkyl, $R_2$ represents in each case 5- to 8-membered, lower alkyleneamino, lower alkenyleneamino, aza-lower alkyleneamino, N'-lower alkylaza-lower alkyleneamino, aza-lower alkenyleneamino, N'-lower alkylaza-lower alkenyleneamino, oxa- or thia-lower alkyleneamino, isoindol-2-yl, isoindolin-2-yl, indolin-lyl or indol-1-yl, and $R_a$, $R_b$ and $R_c$ each represents, independently of one another, hydrogen, lower alkyl, hydroxy-lower alkyl, halo-lower alkyl, lower alkenyl, lower alkoxy, lower alkylthio, lower alkanesulphinyl, lower alkanesulphonyl, hydroxy, halogen, lower alkanoyloxy, lower alkanoyl, or nitro, or $R_a$ together with $R_b$ represents 3- or 4-membered alkylene, and $R_c$ has the meanings given above for $R_c$, and their salts, and isomers.

4. The method according to claim 3 wherein $R_1$ represents hydrogen or lower alkyl having up to and including 4 carbon atoms, $R_2$ represents 5- to 8-membered lower alkyleneamino having from 4 to 10 carbon atoms, 5- to 8-membered lower alkenyleneamino having one or two double bonds and from 4 to 10 carbon atoms, monooxa-lower alkyleneamino having from 4 to 7 carbon atoms, indolin-1-yl or indol-1-yl, and $R_a$ and $R_b$ each represents, independently of the other, hydrogen, lower alkyl, or halogen, or $R_a$ and $R_b$ together represent 3- or 4-membered alkylene, and $R_c$ represents hydrogen, and their salts, and isomers.

5. The method according to claim 3 wherein $R_1$ represents hydrogen or lower alkyl having up to and including 4 carbon atoms, $R_2$ represents 1-pyrrolyl, 4-morpholinyl, 3-pyrrolin-1-yl, or unbranched 4- to 6-membered alkyleneamino, $R_a$ and $R_c$ each represents hydrogen and $R_b$ represents hydrogen, lower alkyl having up to and including 4 carbon atoms, or halogen having an atomic number of up to and including 35, or $R_c$ represents hydrogen and $R_a$ and $R_b$ together represents 3- or 4-membered alkylene, or one or the radicals $R_a$ and $R_b$ represents halogen having an atomic number of up to and including 35, and the other represents lower alkyl having up to and including 4 carbon atoms, and their salts, and isomers.

6. The method according to claim 3 wherein $R_1$ represents lower alkyl having up to and including 4 carbon atoms, $R_2$ represents 5- to 8-membered lower alkenyleneamino, $R_a$ and $R_c$ represent hydrogen and $R_b$ represents lower alkyl having up to and including 4 carbon atoms, and their salts and their isomers.

7. The method according to claim 1 wherein the compound is 5-chloro-3-methyl-6-morpholinobenzofuran-2(3H)-one or a salt or isomer thereof.

8. The method according to claim 1 wherein the benzofuran is 5-chloro-3-methyl-6-(piperidin-1-yl)-benzofuran-2(3H)-one or a salt or isomer thereof.

9. The method according to claim 1 wherein the benzofuran is 5-chloro-3-methyl-6-(pyrrol-1-yl)-benzofuran-2(3H)-one or a salt or isomer thereof.

10. The method according to claim 1 wherein the benzofuran is 3,5-dimethyl-6-(piperidin-1-yl)-benzofuran-2(3H)-one or a salt or isomer thereof.

11. The method according to claim 1 wherein the benzofuran is 3,5-dimethyl-6-(pyrrol-1-yl)-benzofuran-2(3H)-one or a salt or isomer thereof.

* * * * *